United States Patent [19]

Norcross et al.

[11] 4,425,330

[45] Jan. 10, 1984

[54] BOVINE MASTITIS VACCINE AND METHOD FOR DETECTING EFFICACY THEREOF

[75] Inventors: Neil L. Norcross; Johanna P. Opdebeeck, both of Ithaca, N.Y.

[73] Assignee: Cornell Research Foundation, Inc., Ithaca, N.Y.

[21] Appl. No.: 265,287

[22] Filed: May 20, 1981

[51] Int. Cl.³ .................. A61K 39/09; A61K 39/085
[52] U.S. Cl. ........................................ 424/92; 424/88
[58] Field of Search ..................... 424/92, 88

[56] References Cited

U.S. PATENT DOCUMENTS 4,197,290 4/1980 Yoshida .................................. 424/92
4,207,414 6/1980 Kasper .................................. 424/92

*Primary Examiner*—Blondel Hazel
*Attorney, Agent, or Firm*—Jones, Tullar & Cooper

[57] ABSTRACT

This invention relates to a vaccine for the prevention and/or control of gram-positive cocci, e.g. *Str. agalactiae* and *S. aureus,* induced bovine mastitis infections and to an immunological method, an enzyme linked immunosorbent assay (ELISA), for assaying the humoral immue response of the lactating bovine mammary gland to detect antibody variables associated with the vaccinated or suspected infected bovine.

6 Claims, 8 Drawing Figures

⊂⊃  Staphylococcal somatic antigen or staphylococcal alpha hemolysin.

⊱  Specific milk Ig.

⊱–o  Peroxidase conjugated rabbit anti-bovine IgG (heavy and light chains).

o  Hydrolyzed substrate.

FIG. 2-1.
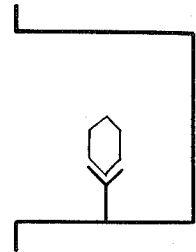
FIG. 2-2.
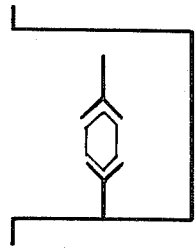
FIG. 2-3.
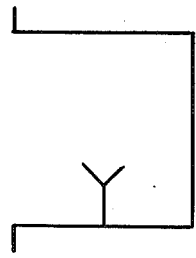
FIG. 2-4.
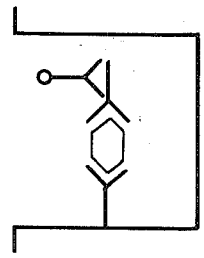
FIG. 2-5.
Y  Rabbit anti-streptococcal Group B and type III Igs.
◯  Streptococcal Group B and type III antigen.
⅄  Specific milk Ig.
⅄ (with o)  Peroxidase conjugated rabbit anti-bovine IgG (heavy and light chains).
o  Hydrolyzed substrate.

BOVINE MASTITIS VACCINE AND METHOD FOR DETECTING EFFICACY THEREOF

BACKGROUND OF THE INVENTION

Bovine mastitis, an inflammation or an infection of the bovine mammary gland or udder is a serious problem to the fluid milk industry. Various microorganisms are associated with mastitis. However, a large proportion of these intramammary infections are caused by gram-positive cocci and specifically *Streptococcus agalactiae* and *Staphylococcus aureus.* Treatment and prophylactses of mastitis encompasses milking machine management, test hygiene and antibiotic therapy. Vaccination has been attempted in numerous reports (see, for example, Schalm et al: "Bovine Mastitis", Lea & Febeger, Philadelphia, Pa., 1971 and Janovics et al, *Jour. So. Afric. Vet. Assoc.,* 48:155–161 (1977)). These attempts have meet with mixed success and failure, but have never given protection adequate to base a sound control program upon their economical use. Likewise no assay existed based upon which knowledgable decisions as to vaccination efficacy and duration could be based.

A significant review of the status of bovine mastitis research, as of 1977, in Volume 170 J.A.V.M.A. wherein the entire volume reports papers given in a colloquum on bovine mastitis.

IMMUNOGLOBULINS OF THE MAMMARY GLAND

The lactating cow produces very low levels of immunoglobulin (Ig) in milk. Milk one month post partum contains approximately 1/40th the total Ig level of serum and 1/80th that of colostrum [Norcross, *J.A.V.-M.A.,* 170:1228–1231 (1977)].

In contrast with species such as man and pig, where IgA is the major secretory Ig [Butler, *J.A.V.M.A.,* 163:794–98], IgG is the class found in the greatest concentration in bovine milk. This feature is a function of the selective transfer of $IgG_1$ from blood into lacteal secretions [Lascelles et al, "Localized Humorel Immunity with Particular Reference to Ruminants," 170–208 (1979); Lascelles, "The Immune System of the Ruminant Mammary Gland and Its Role in the Control of Mastitis," 62:154–160 (1979); Butler et al, *J. Immunol.,* 109:38–46 (1978)]. In serum the relative ratios of $IgG_1$ to $IgG_2$ are 2:1. In milk mainly as a result of the selective transfer, this ratio becomes 10–15:1 [Butler, *J.A.V.M.A.,* 163:795–98; Norcross, *J.A.V.M.A.,* 170:1228–81 (1979)]. The selectivity of this mechanism is thought to be based on a sepcific receptor system on the alveolar epithelial cell. Actual transfer across the cell into the alveolar lumen is by means of a pinocytotic vesicular system [Lascelles (1979), supra.].

IgA, IgM and also some $IgG_1$ are produced locally within the mammary gland itself [Chang et al, *Am. J. Vet. Res.,* 41:1416–18; Butler et al, *J. Immunol.,* 109:38–46 (1972)]. Cells producing IgA have been identified in the gland by means of anti-IgA serum labelled with fluorescein isothyiocyanate [Johnson, "Immunologic studies of streptococcus agalactiae in the bovine mammary gland", MS thesis, Ithaca, NY (1976)]. The Jerne plaque assay has also been used to demonstrate the presence of antibody producing cells in lacteal secretions. Chang et al indicated that in non-lactating cows, IgA and $IgG_1$ producing cells represented the most significant fractions of the local Ig synthesis [Chang et al, *Amer. J. Vet. Res.,* 41:1416–18)].

Defense of the Mammary Gland Against Mastitis Pathogens

The mammary glands defense against Gram positive cocci, with particular reference to *Staphylococcus aureus* and *Streptococcus agalactiae,* is based on a major humoral component [Reiter et al, *IDF Bulletin Doc.,* 85:210–22 (1975); Norcross, *J.A.V.M.A.,* 170:1228–31 (1977)].

Specific adherence of bacteria to mucous membranes is an important feature in the pathogenesis of these two bacteria [Frost et. al, *Infect. and Immun.,* 15:245–53 (1977) and 12:1154–56 (1975)].

Antibodies of the IgA class function to prevent this adherence. Other classes of antibodies, in particular IgM, are probably also involved in preventing adherence by means of mechanisms such as agglutination. IgA antibodies may conceivably be the principle inhibitors of bacterial adherence by virtue of their dominant concentration in most of the secretions investigated [Winter, *Advances in Vet. Sci. and Compar. Med.,* 12:53–69 (1979)].

IgG antibodies in milk function primarily as opsonins, in preparation for the phagocytosis of pathogens by macrophages and polymorphonuclear leucocytes (PMN). These cells carry specific receptors for the Fc fragment of certain IgG subclasses. McGuire, considering the differences of bovine IgG subclasses 1 and 2 in relation to their interaction with complement, macrophages and neutrophils, concluded that under disease situations it is likely that the functional properties of these two subclasses are similar [McGuire et al, *Immunol.,* 38:249–56 (1979)]. There is evidence that opsonins are essential for the phagocytosis of S. aureus [Kapral, *N.Y. Acad. Sci. Ann.,* 128:285–300 (1965); Mudd et al, *Nature,* 199:1200 (1963); Cohn et al, *J.Exp.Med.,* 110:419(1959); Rogers et al, *N.Y. Acad. Sci. Ann.,* 128:274–284(1965)]. *Str. agalactiae* is effectively destroyed following opsoninsation and ingestion by leucocytes. *S. aureus,* however, is capable to an extent of survival with a phagocytic cell. There is, however, no evidence that intracellular replication takes place [Kapral, *N.Y. Acad. Sci. Ann.,* 128:285–300(1965)]. Although intracellular survival may constitute an important pathogenic feature in relation to the survival capabilities of the bacteria, staphylococcal disease is characterized by extracellular replicative mechanisms.

Neutralization of toxins constitutes an important component of the defense mechanisms against the staphylococci [Anderson, *Br. Vet. J.,* 132:229–245 (1976) ]. In the event of colonisation of the host by the bacteria, an effective anti-toxic immunity will lessen the severity of the disease signs [Anderson, *Br. Vet. J.,* 132:229–245 (1976); Derbyshire, *J.Comp.Path.,* 70:222 (1960); Derbyshire et al, *Res. Vet. Sci.* 3:56–62(1962)]. Inactivation of toxins is achieved by an antigen antibody interaction which essentially inhibits effective binding of the toxin to its receptor site on target cells. Antibodies of the IgG class, in particular subclass 1, function most efficiently in neutralization [Winter, *Adv. Vet. Sci. and Compar. Med,* 23:52–69(1979); Ourth, *Immunochem.,* 11:223–225 (1974)].

PMN's play a protective role in the mammary gland [Jain et al, *Amer.J. Vet.Res.,* 32:19–29 (1971); Paape et al, *Amer. J.Vet.Res.,* 36:22:1737–1743(1979); Jain, *J.Dairy Sci,* 62:128–134 (1979)]. There are, however, certain unique features associated with the functions of this cell type in a milk environment. PMN's in milk exhibit an irreversible decreased efficiency in phagocytosis. This is attributable to the fact that the surface of the PMN becomes coated by milk casin and the cell is engaged in phagocytosing casein and fat [Russel et al, *Res.Vet.Sci.,* 20:30-35 (1976); Paape et al, *Amer.J.Vet.Res,* 36:12 1737-1743 (1975)]. In addition, discharging of granules into the casein and fat filled phagolysosomes diverts the defense mechanisms of the cell from pathogens which it may also have ingested. A further factor depressing the efficiency of PMN function in milk is that glucose levels in this medium are deficient, since addition of glucose enhances the phagocytic capabilities of the cells [Newbould, *Can.J.Comp.Med,* 37:189-194 (1973)]. The increase of Ig in milk by means of nonspecific udder inflammation does not give rise to an increased percent of phagocytosis [Guidry et al, *Am.J.Vet.Res,* 41:751-753 (1980)]. However, it is possible to stimulate phagocytosis in a milk medium by the addition of immune sera [Newbould, *Can.J.Comp.Med,* 37:189-194 (1973)]. Furthermore, Guidry et al showed that phagocytosis of *S. aureus* by neutrophils in whey could be increased 62% following immunization [Guidry et al, *J. Dairy Sci.* 60:Supp 1:135 (1977)].

Immunization against mastitis

In order to assay the effectiveness of vaccination, two basic responses have been evaluated. These are first the immunological response of the animal mainly by means of Ig assay, and second the protective efficacy of a vaccine under circumstances of artificial and natural challenge. The effects of both local and systemic routes of immunization have been investigated.

Direct stimulation of the mammary gland has been shown to result in enhanced levels of total Ig in cows [Wilson et al, *Immunol.,* 23:313-320 (1972)]. Following local immunization in the cow, the Ig increase is most evident in the IgA fraction [Hubler et al, *Milchwissenssenshaft.,* 33:1-6 & 101-105 (1978); Wilson et al, *Immunol.,* 23-313-320 & 947-955 (1972)].

Pre-parturient intramammary vaccination carried out by Wilson et al using a live formalin treated *Escherichia coli* vaccine gave rise to an increase in total milk IgA concentrations of up to 3 fold, in comparison with unvaccinated control glands. A difference between the vaccinated and unvaccinated glands was still evident 28 days post partum. The milk also showed evidence of somewhat increased levels of total IgM and IgG [Wilson et al, *Immunol.,* 23:313-320 (1972)].

Sytemic immunization has also been examined as a means for stimulating specific Ig production.

An experiment was carried out on cows, by McDowell and Lascelles to explore the effects of systemic immunization during mammary involution. The rationale for the experiment was based on the following: (1) There is a massive migration of lymphoid cells into the mammary gland at drying off, (2) Lymphoid cells from lymph nodes which have been stimulated by antigens migrate to tissues and organs and subsequently systhesize antibodies there. A *Salmonella typhi* bacterin was administered by means of 2 routes and combinations thereof. These included local stimulation, local and sytemic combined, and sytemic alone with and without the addition of a mineral oil adjuvant. Sytemic administration was by means of intramuscular injection. Local administration was by means of instillation through the teat orifice into the gland. A combined systemic-local stimulus gave a significantly greater antibody response in milk, as measured by bacterial agglutination, than either of the 2 methods alone. The response to the systemic stimulus was greatly enhanced by the addition of the adjuvant preparation. The class of antibody involved in the immune response was almost exclusively IgA and IgM. This was true for all the combinations of routes for immunization. The authors suggested that this may be due to migration of stimulated lymphoid cells to the gland at involution where as sessile entities they secrete antibody, or alternatively, antigens may be carried to the gland and prime IgM and IgA producing cells in situ [Brock et al, *Res.Vet.Sci.,* 19:152-158 (1975)].

Brock et al, using an *S. aureus* bacterin, inoculated dry cows. The vaccine was administered in Freunds complete adjuvant by intramuscular injection and also directly into the quarter, through the udder wall. In addition, it was instilled through the teat orifice into the gland without the adjuvant. The results indicated that although the level of agglutinins in the serum increased slightly, milk and colostrum agglutinins were not increased when compared to the controls. Total levels of all classes and subclasses of Ig in serum, colostrum or milk were not elevated [Brock et al, *Res.Vet.Sci.,* 19:152-158 (1975)].

Blobel & Berman in 1962 administered a high dose vaccine to cows using an extremely intensive schedule. *S. aureus* strain 280 as a bacterin, its hemolysins, coagulase and potassium aluminum sulfate as an adjuvant were administered 3 times at 15 day intervals. This was followed by 4 booster injections 3 to 5 months apart. For transient periods of time, milk levels of anti-alpha and beta hemolysins in amounts of up to 4 I.U. per ml were reported. These milk antibodies were found only in certain individual high responding cows and only in association with serum levels exceeding 32 I.U. per ml [Blobel et al, *Amer.J.Vet.Res.,* 23:92 (1962)].

In parallel with the work carried out to evaluate the antibody response of the mammary gland to immunization, there has been a great deal of investigation into the practical efficacy of various vaccines. Both natural and artificial means of exposure to challenge have been employed. The results reported are conflicting as to the protective value of mastitis vaccination.

In the early 1960's, Derbyshire reported a series of trials in goats, and also in cows, in which he used *S. aureus* cell-toxoid vaccines, adjuvanted with aluminum hydroxide gel. Challenge with $10^9$ staphylococci of certain homologous strains showed that the vaccine was effective to the point of a "mild transient reaction" occurring in vaccinates as opposed to an acute gangrenous mastitis on controls [Derbyshire, *J.Comp.Path.,* 70:222-231 (1960)]. Challenge of vaccinated animals in a subsequent experiment with heterologous strains (BB, N90 and S20) failed to provide significant protection [Derbyshire, *J.Comp.Path.,* 71:146-158 (1961)]. *S. aureus* strain BB is a particularly virulent strain isolated from bovine mastitis causing an acute gangrenous reaction [Brock et al, *Res.Vet.Sci,* 19:152-158(1975)]. Vaccination with this strain was not successful in providing any protection to homologous challenge [Derbyshire, *J.Comp.Path,* 70:222-231 (1960)]. However, later Derbyshire reported some success against challenge with strain BB (again a less severe clinical reaction) using a vaccine containing α hemolysin, coagulase and leucocidin [Derbyshire et al, *Res. Vet. Sci,* 3:56-62 (1962)].

Brock et al inoculated cows with a formolised *S. aureus* bacterin by systemic and intramammary routes. Three strains were used (BB, Mexi and 3528). The cows were challenged with 10 CFU of 2 homologous strains. Of 22 quarters challenged with Mexi strain, 9 resisted infection. Of 24 quarters challenged with BB strain, 2 resisted [Brock et al, *Res. Vet. Sci,* 19:152-158 (1975)].

Further challenge exposure experiments were reported by Norcross. Lactating cows were inoculated in the region of the external inguinal lymph node with formolised *S. aureus* strain 305 bacterin and its toxoid. Of 20 glands exposed to 15 CFU of a strain 305, 85% were resistant. Control cows showed 100% infection with this dose. A second experiment yielded less positive results in that only 50% of glands challenged were resistant [Norcross, *J.A.V.M.A.* 170:1228-1231 (1977)].

Field trials of staphylococcal and streptococcal vaccines have been reported [Johnson et al, *Corn. Vet.* (1970); Slanetz et al, *Am.J.Vet.Res,* 24:102:923-931 (1963); Derbyshire et al, *Vet.Rec,* 75:46:1208-1210 (1963); Blobel et al, *Amer.J.Vet.Res,* 23:92 (1962)]. In these trials, the mode of challenge relies on the natural spread of infection within the herd.

Slanetz et al [Slanetz et al, *Am.J.Vet.Res,* 24:102:923-931(1963)] and Blobel and Berman [Blobel et al, *Amer.J.Vet.Res,* 23:92 (1962)], reported a decrease in new intramammary infections and a decrease in clinical severity of the disease in cows vaccinated with an *S. aureus* vaccines. Conversely, Derbyshire and Edwards in 1963 reported that a field trial of a staphylococcal celltoxoid vaccine yielded results which indicated that the vaccine was ineffective in decreasing either new intramammary infections or reducing the severity of the disease [Derbyshire et al, *Vet.Rec,* 75:46:1208-1210 (1963)].

It appears from the data presented on vaccination, that the cow is capable of an immune response in the mammary gland. It is possible to elevate the levels of Ig in milk and to stimulate a response of a specific nature. At a practical level, mastitis vaccination is at least partially effective in preventing the establishment of new infections, but more commonly has been associated with decreasing the severity of the disease. One of the factors which has contributed to the essential inadquacy of vaccination under field conditions is that the area pertaining to the ingredients necessary for an effective vaccine has been insufficiently investigated, in terms of the response of the gland itself.

The methods available for detection of a specific immune reaction in the lactating gland have been inadequate with respect to sensitivity, specificity and discernment of Ig class involved in the response. Consequently, there is no information available on the immunogenicity of various antigens and preparation of these antigens in relation to their effects on the gland. Certainly it is not valid to extrapolate that the systemic immunological response to a vaccine is applicable in the lactating mammary gland.

DESCRIPTION OF THE INVENTION

This invention relates to a vaccine for the prevention and/or control of gram-positive cocci, e.g. *Str. agalactiae* and *S. aureus,* induced bovine mastitis infections and to an immunological method. An enzyme linked immunosorbent assay (ELISA) for assaying the humoral immune response of the lactating bovine mammary gland to detect antibody variables associated with the vaccinated or suspected infected bovine.

The vaccine of the invention comprises a mixture of active ingredients in combination with a specific adjuvant. Experimental results indicate that adjuvant substantially enhances the efficacy of the vaccine over the efficacy of the same active ingredients, alone or in combination with other previously suggested adjuvants. Likewise, the use of optional amounts of the active ingredients in conjunction with the adjuvant enhances efficacy of the vaccine.

The vaccine of the invention comprises an active ingredient component containing per dose (a) in total combination a bovine mastitis preventing or controlling amount of at least one *S. aureus* somatic antigen which is an encapsulated antigen derived from a bovine isolated inactivated *S. aureus* usually in an amount sufficient to contribute at least about 25, preferably between about 100-120 and usually not more than about 425 mg N per dose; the presently preferred antigen being one derived from *S. aureus* strain NL6 (ATCC 31885);

(b) in total combination a bovine mastitis preventing or controlling amount of at least one unencapsulated *S. aureus* antigen which is derived from a bovine isolated inactivated *S. aureus* usually in an amount sufficient to conribute at least about 25, preferable between 100-120 and usually not more than about 425 mg N per dose; the presently preferred antigen being at least one or more preferably antigen derived from both of *S. aureus* strains IR1 (ATCC 31886) and T33 (ATCC 31887);

(c) in total combination a bovine mastitis preventing or controlling amount of staphylococcal α hemolysin toxoid, usually in an amount sufficient to contribute at least about 0.5, preferably between about 0.8-1.2 and usually not more than about 2 mg N per dose; the presently preferred α hemolysin toxoid being derived from *S. aureus* strain Wood 46 (ATCC 10832);

(d) in total combination a bovine mastitis preventing or controlling amount of staphylococcal β hemolysin toxoid, usually in an amount sufficient to contribute at least about 1, preferably between 1.3-1.7, and usually not more than about 2.5 mg N per dose; the presently preferred staphylococcal β hemolysin toxoid being derived from *S. aureus* strain SS 697 (ATCC 31888);

(e) in total combination a bovine mastitis preventing or controlling amount of staphylococcal γ hemolysn toxoid, usually in an amount sufficient to contribute at least about 0.5, preferably between about 0.8-1.2, and usually not more than about 2 mg N per dose; the presently preferred γ hemolysin toxoid being derived from *S. aureus* strain 5R (ATCC 31889);

(f) in total combination a bovine mastitis preventing or controlling amount of staphylococcal derived Leucocidin toxoid, usually in an amount sufficient to contribute at least about 1, preferably between 1.3-1.7, and usually not more than about 2.5 mg N per dose; the present source for obtaining Leucocidin being *S. aureus* strain P83 (ATCC 31890); and (g) in total combination a bovine mastitis preventing or controlling amount of at least one of *Str. agalactiae* antigen derived from a bovine isolated inactivated *Str. agalactiae;* the antigen being derived from at least one and preferably mixtures, preferably of all three of inactivated *Str. agalactiae,* Type I (Ia or Ib or Ic or mixtures, preferably all three of Ia, Ib and (c), Type II and Type III; the total amount of each of said *Str. agalactiae* antigen present usually being an amount sufficient to contribute at least about 17, preferably between about 60–80, and usually no more than about 280 mg N per dose.

While the preferred vaccine, for broad applicability, contains effective amounts of each of the above-listed components, useful vaccines can be provided where only one or at least less than all of the bactrins and/or toxoids are employed. Particularly useful vaccines, especially adapted for a specific locale can be adapted where the causative agent or agents have been isolated and the materials used, tailored to combat that agent or the manifestations of the disease caused thereby. Likewise the antigens employed may even be derived from cultures of the specific bacteria present.

As employed herein "in total combination a bovine mastitis preventing or controlling amount" is that amount of an active material when used in conjunction with the other active materials enumerated above and present which prevents infection and/or reduces the clinical manifestations of the diseases, for example reduces bacteria cell counts in the milk and or physiological manifestations in the bovine as compared for example to a control group.

The vaccine of the invention comprises the above active ingredients in aqueous dispersion (typically about 2 to 4 ml, preferably about 2.5 ml, per dose) emulsified with sufficient mineral oil, preferably together with emulsion enhancing amounts of a physiologically acceptable emulsifying agent, to provide enhnaced vaccine response in the animal. Oily adjuvants comprising mineral oil and emulsifiers such as mannide monooleate and lanolin are known in the art as incomplete Freund's adjuvants and are known in certain cases to enhance vaccine efficacy [see for example British Veterinary Codex 1965, Supplement 1970, pages 83–86]. A presently preferred incomplete Freund's adjuvant useful in the vaccines of the invention is Difco Adjuvant comprising 15% Arlacel A (mannide monooleate) and 85% Bayol F (paraffin oil).

As previously stated, the amount of mineral oil employed is at least that amount necessary to obtain enhanced vaccine efficacy, and should be an amount which forms an emulsion which remains sufficiently stable so as not to significantly separate for several hours after mixing. If separation does occur between mixing and use, typically the layers may be reemulsified by vigorous agitation prior to use. Typically about equal volumes of aqueous active materials and mineral oil with an emulsion enhancing amount of an emulsifier are employed to form reasonably stable useful emulsion, although volume ratios of 1:4 to 4:1 may be employed, for example.

The water-in-oil emulsion vaccines of the invention are administered to a bovine in bovine mastitis preventing or controlling amounts, preferably in at least two time sequenced doses, preferably separated by one to four, preferably about three weeks. The vaccine is administered by systemic injection, other than orally or intraveneously, preferably by injection in the vicinity of a lymph node, most preferably the external inguinal lymph node.

In addition to the above vaccine, the invention also relates to the use of enzyme linked immunoassay in the control of bovine mastitis to detect the presence of or change in levels of specific antibody of each immunoglobulin class associated with immunity to bovine mastitis provided by the above-described vaccine in the milk of vaccinated bovine.

The enzyme linked immunoassay of the invention in one aspect (FIG. 1) comprises absorbing staphylococcal antigens on a solid phase and removing unabsorbed material; contacting the absorbed antigen with a defatted bovine milk sample to absorb staphylococcal antibodies if present in the milk and removing unabsorbed material; contacting the resultant absorbed material with an enzyme conjugated species specific anti IgG serum, specific to a particular staphylococcal antibody sought to be measured to react with the absorbed ataphylococcal antibody and removing unabsorbed materials; contacting the resultant absorbed material with a reactive substrate which yields a measurable reaction product and measuring the measurable reaction product thereby indirectly determining the amount of the specific staphylococcal antibody, wought to be detected, absorbed on the substrate.

The enzyme linked immunoassay of the invention in another aspect (FIG. 2) comprises absorbing anti-streptococcal Ig on a solid phase and removing unabsorbed material; contacting the absorbed anti-streptococcal Ig with streptococcal antigen to form a conplexed antigen-antibody and removing unabsorbed material; contacting the absorbed antigen-antibody complex with a defatted bovine milk sample to absorb streptococcal antibodies if present in the milk and removing unabsorbed material; contacting the resultant absorbed material with an enzyme conjugated species specific anti IgG serum, specific to a particular streptococcal antibody sought to be measured, to react with the absorbed streptococcal antibody and removing unabsorbed material; contacting the resultant absorbed material with a reactive substrate which yields a measurable reaction product thereby indirectly determining the amount of the specific streptococcal antibody, sought to be detected, absorbed on the substrate.

Figure 1:
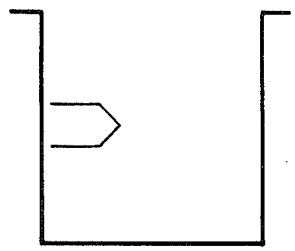
FIG. 1 is a schematic representation of an indirect ELISA for detection of milk IgG specific for staphylococcal somatic antigen and staphylococcal alpha hemolysin.

EXAMPLE I
Elisa Test

An indirect ELISA test system was considered for adaptation for the staphylococcal antigens [Voller et al, "The enzyme linked immunosorbent assay (ELISA)", Dynatech Europe, Borough House, Rue du Pre, Guernsey, G. B. (1979)] illustrated in FIG. 1. Essential principles are as follows: Antigen is adsorbed by incubation to a solid phase, unabsorbed antigen being removed by washing. Samples to be evaluated for antibody are added and incubated. Antibody which has not reacted with the antigen is washed out, and an enzyme conjugated, species specific, anti-IgG serum is added and incubated. Unreacted conjugated antiserum is again removed by washing and a substrate is added. The substrate is hydrolyzed by the enzyme, if present, resulting in a color change which may be read spectophotometrically. The degree of substrate hydrolysis is directly proportional to the amount of antibody bound to the antigen.

Streptococcal Group and type antigens are carbohydrate in nature and adsorb poorly to the polystyrene solid phase. A modified ELISA system was therefore considered for use with the streptococci. This system is illustrated in FIG. 2. It is an adaptation of the method described by Voller et al for the measurement of antigen [Vollet et al, supra.]. The essential modification here is the addition of a step which involves initial adsorption of antistreptococcal Group B and type III Igs to the solid phase followed by washing, addition of antigen and incubation. The complexed antigen-antibody then forms the antigen phase for the test. The remainder of the test is carried out as described previously for the indirect method.

MATERIALS AND METHODS
Bacterin-toxoid preparation

*S. aureus* strain 305 was grown in trypticase soy broth (Becton, Dickinson, and Co., Cockeysville, MD) for 18 hours, centrifuged, washed with sterile saline, and inactivated bacteria were washed and resuspended in sterile saline, and inactivated by suspension in 0.3% formolized saline for 5 days at 25° C. the inactivated bacteria were washed and resuspended in sterile saline. The final concentration of bacteria in the inoculum was $1.8 \times 10^8$ cells per ml.

Staphylococcal alpha hemolysin was produced using *S. aureus* strain 305 following the method described by Coulter.

Purification was carried out by extraction using 0.15 M sodium acetate [Coulter, *J.Bacteriol*, 92:1655-1662(1966)]. This preparation contained 24 I.U. of hemolytic activity per ml. by comparison with a standard staphylococcal α hemolysin preparation (Burroughs Wellcome, Greenville, NC). Following filtration using a 0.45 micron pore size filter (Nalge Co., Rochester, N.Y.) the toxin was inactivated by 30 minutes incubation in a water bath at 60° C. The final concentration of α hemolysin in the inoculum was 2.4 I.U. per ml.

Animals

Nine lactating Holstein Friesian cows were randomly allocated to two groups of 6 and 3 animals each. Clinical evaluation revealed no evidence of udder inflammation. *S. aureus* was not isolated from lacteal secretions. Table 2 outlines the lactation status of the animals.

TABLE 2
Lactation status of the experimental animals.

| Cow Number | Lactation Number | Days Postpartum on Day 0 of Experiment |
|---|---|---|
| Group I[a] | | |
| 2022 | 4 | 10 |
| 1902 | 3 | 21 |
| 1586 | 4 | 28 |
| 2228 | 2 | 28 |
| 1964 | 3 | 26 |
| 2036 | 2 | 14 |
| Group II[b] | | |
| 1635 | 4 | 16 |
| 2004 | 3 | 39 |
| 1934 | 3 | 31 |

[a]Group I: Experimental animals subjected to bacterin-toxoid stimulation.
[b]Group II: Control animals receiving saline.

Immunization Procedure

The 6 cows which received antigen were inoculated with 10 ml of the preparation described above on days 0, 4, 8, 12, 16 and 20 of the experiment. Immunization, by means of an 18 gauge 1½ inch needle, was in the region of the external inguinal lymph node, alternating between the right and the left. The 3 control animals received 10 ml of sterile saline using the same regime.

Sampling Procedure

Milk samples were taken aseptically from all four quarters of each cow, prior to and at intervals following immunization. All samples were taken before evening milking. Following microbiological culture of each quarter, the samples were centrifuged at 300 g for 15 minutes and the milk was aspirated from below the fat layer. Composite samples were made up for each cow, which represented all four quarters. Samples were stored at −20° C.

Microbiological Culture

Approximately 0.1 ml of each quarter sample was plated on an esculin bovine blood agar plate and incubated at 37° C. for 24 hours. Microbiological identification was based on colony morphology, hemolytic pattern, Gram strain and where relevant, the CAMP test and the tube coagulase test ["Microbiological procedures for the diagnosis of bovine mastitis", National Mastitis Council, Washington, D.C., University of New Hampshire Press (1969)].

Hemolytic Assay

Hemolytic assays were carried out on the milk samples using staphylococcal α hemolysin (Burroughs Wellcome, Greenville, NC) and 2% washed sheep red blood cells. The method employed was that described by Burroughs Wellcome. Anti-staphylococcal α hemolysin (Burroughs Wellcome, Greenville, NC) was used as a control.

Preparation of Antigens for ELISA

Staphylococcal α hemolysin was produced as described previously in the preparation of the bacterin-toxoid.

*S. aureus* strain 305 (ATCC 29740) was used to produce staphylococcal somatic antigen. An 18 hour culture was grown, harvested, and washed as described previously in the preparation of the bacterin-toxoid. The organisms harvested from two liters of culture media were suspended in 50 ml of sterile saline and subjected to 30 minutes of ultrasonic disruption. A Model S220 sonifier (Branson Instruments Inc., Danbury, CT) with a maximum probe size, at maximum energy settings was used for this purpose. The bacterial suspension was maintained below 30° C. by means of an icebath, throughout the procedure. Following insonation, the preparation was centrifuged at 1700 g for 45 minutes and the resulting pellet was discarded.

*Str. alagactiae* type III was grown in Todd Hewitt broth (Difco Laboratories, Detroit, Mich.), which was modified according to Baker et al [Baker et al, *J.Exper.Med.*, 143: 258–270 (1976)]. The organisms were harvested by centrifugation at 1700 g and washed in sterile saline. The streptococcal group and type antigen was extracted using the neutral buffer method described by Baker et al for the preparation of "native" type III antigen [Baker at al, *J.Exper.Med.*, 143: 258–270 (1976)]. This preparation contained both Group B and type III immunoligical activity on microimmunodiffusion.

The 3 antigen preparations were filtered using 0.45 micron pore size filters (Nalge Co., Rochester, NY) and subsequently dialyzed against 0.06 M carbonate buffer pH 9.6 [Slanetz et al, *Am.J.Vet.Res*, 26:688–695 (1965)].

Protein and Carbohydrate content of ELISA antigens

Protein content was determined as mg N/ml by means of Kjeldahl nitrogen determination [Baker et al, *J.Exper.Med*, 143: 258–270 (1976)]. Carbohydrate content was determined by the Indole test using ug glucose/ml as a standard [Williams et al, "Methods in immunology and immunochemistry," II Acad. Press, NY, p. 187 (1968)].

General ELISA Procedures

ELISA was performed by adaptation of the basic procedure guidelines described by Bullock and Walls [Bullock et al, *J.Infect.Dis.*, 136: Supplem. Oct. 1977]. The tests were carried out using an EIA automatic analyzer (Gilford Instrument Laboratories Inc., Oberlin, OH). The solid phase used was a polystrene cuvette system (Gilford Instrument Laboratories Inc., Oberlin, OH) which consisted of 10 wells in 5 cuvette strips.

The buffer for coating the cuvettes with antigen was 0.06 M carbonate buffer pH 9.6 ($CO_3$ buffer).

Coating with antigen was carried out by 4 hour incubations at 37° C. followed by storage of plates overnight at 40° C. All incubations in the test were carried out in air incubator at 37° C.

Washing throughout the procedure was carried out by 5 washes using 0.01 M phosphate buffered saline, pH 7.2, containing 0.5% Tween 20 (PBS-T) (Fisher Scientific Co., Fair Lawn, NJ).

Enzyme conjugated antisera used were the IgG fractions of anti-species IgG (heavy and light chains) conjugated with the enzyme peroxidase (Capel Laboratories, Cochranville, PA).

The substrate for the enzyme was 2,2'-Azino-di-(3-ethyl-benzthiazoline-6-sulphonic acid) (ABTS) (Sigma Chemical Co., Saint Louis, MO) prepared according to the method described by Saunders et al [Saunders et al, Los Alamos Sci. Lab. Univ. Calif. Prog. Rep: LA-7078-PR-1 (1978)]. The substrate was dispensed and the plate was shaken for 30 seconds on a Cooke micro-shaker (Dynatch Laboratories, Inc., Alexandria, VA). The degree of substrate catalysis was determined by reading absorbance at 405 nm. A constant interval of 5 minutes was allowed to elapse between dispensing of substrate and reading of each individual sample.

The standard volume of all reagents in the test was 0.4 ml unless otherwise specified.

Titration of ELISA antigens

Chequer board titration of the staphylococcal and streptococcal antigens were carried out in an ELISA system in order to determine the optimal antigen concentrations to be used in subsequent tests [Voller et al, "The enzyme linked immunosorbent assay (ELISA)", Dynatech Europe, Burrough House, Rue du Pre, Guernsey, B. G. (1979)].

Titration of the 2 staphylococcal antigens was carried out in an indirect test system. Serial dilutions of each antigen were made in $CO_3$ buffer, added in repeating vertical rows to the cuvette wells, and incubated for 4 hours at 37° C. and sorted overnight at 4° C. The cuvettes were then washed. Reference positive sera from hyperimmunized rabbits was serially diluted in PBS-T and added to the cuvette wells in repeating horizontal rows. Each serum dilution was therefore reacted with each antigen dilution. Incubation was for 40 minutes. Following washing, peroxidase conjugated IgG fraction of goat antirabbit IgG (heavy and light chains) (Cappel Laboratories, Cochranville, PA) was added to each well as a solution of 1:500 in PBS-T and incubated for 40 minutes. Unreacted conjugated antisera was washed out. The substrate was added and evaluated as described above for General ELISA Procedures.

The streptococcal group and type specific antigen is carbohydrate in nature and did not adhere to polystyrene cuvettes as readily as the staphylococcal protein antigens. In order to optimize adsorption of the streptococcal extract antigen, it was necessary to adapt the modified couble antibody sandwich ELISA described by Voller et al for measurement of antigen [Voller et al, "The enzyme linked immunosorbent assay (ELISA)", Dynatech Europe, Borough House, Rue du Pre, Guernsey, G. B. (1979)]. Antibodies to the Group B, type III antigens were raised in rabbits by hyperimmunization with a bacterin following the method described by Lancefield et al [Jour. Exper. Med. 59:441–449 (1934)]. Igs were precipitated from this serum with 35% saturated ammonium sulfate [Hebert et al, *App.Micro.*, 25:26–36 (1972)]. The precipitated Igs were serially diluted in the $CO_3$ buffer, added in repeating vertical rows to the cuvette wells and incubated for 4 hours. The cuvettes were washed and streptococcal extract antigen, serially diluted in PBS-T was added to the cuvette wells in repeating horizontal rows. Each Ig dilution was therefore reacted with each antigen dilution. Incubation for 1 hour was followed by washing.

Reference positive antiserum from hyperimmunized guinea pigs was added to each cuvette well at a dilution of 1:50 in PBS-T. A further 1 hour incubation was again followed by washing. Peroxidase conjugated IgG fraction of goat-anti-guinea pig IgG (heavy and light chains) (Cappel Laboratories, Cochranville, PA) diluted a:500 in PBS-T was added to each well and incubated for 40 minutes. Unreacted conjugated antisera was washed out. The substrate addition and evaluation was carried out as described above for General ELISA Procedures.

ELISA Procedure for Assaying Milk Antibody

Figures 1, 2:
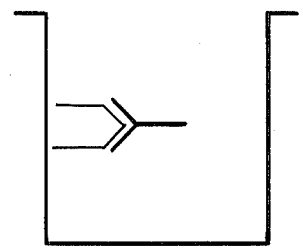
FIG. 2 is a schematic representation of a sandwich ELISA for detection of milk IgG specific for streptococcal Group B and type III antigens.

The test system for the staphylococcal antigens (somatic and α hemolysin) was indirect as illustrated in FIG. 1. The staphylococcal antigens, diluted in $CO_3$ buffer at predetermined optimal concentrations, were adsorbed to the cuvette wall by means of a 4 hour incubation followed by overnight storage at 4° C. Milk samples to be assayed were diluted in PBS-T either serially or at a dilution of 1:6. Three tenths of an ml of these samples were incubated in the antigen coated washed wells for 40 minutes.

Following washing, peroxidase conjugated IgG fraction rabbit anti-bovine IgG (heavy and light chains) (Cappel Laboratories, Cochranville, PA) diluted 1:500 in PBS-T was dispensed into each well and incubated for 40 minutes.

After a final wash, substrate was dispensed and evaluated as described under General ELISA Procedures.

The test system for the streptococcal Group B type III extract antigen was modified double antibody sandwich ELISA as illustrated in FIG. 2. The precipitated Igs containing specifically for streptococcal group and type antigens were diluted to the predetermined optimal concentration in $CO_3$ buffer and adsorbed to the cuvette wells by means of a 4 hour incubation followed by overnight storage at 4° C. Streptococcal Group B, type III antigen was added diluted to the predetermined optimal concentration in PBS-T and incubated for 40 minutes. The test was carried out subsequently as described above.

All milk samples were subjected to 4 analyses and results are expressed as the mean.

RESULTS

Microbiological culture

*S. aureus* was not isolated from any sample during the experimental period. Streptococcus species other than *Str. agalactiae* were isolated intermittently during the experiment.

Hemolytic assay

The hemolytic assays on the milk samples were insufficiently sensitive to allow for reading of a titre.

Protein and carbohydrate content of ELISA antigens

The protein and carbohydrate content of each antigen as used in the ELISA system are shown in Table 3.

TABLE 3

Protein and carbohydrate content of antigens as used in ELISA

| Antigen | Dilution in Carbonate Buffer[a] | mg N/ml[b] | Carbohydrate μg/ml[c] |
|---|---|---|---|
| 1. Staphylococcal somatic antigen | 1:50 | 0.142 | 8 |
| 2. Staphylococcal alpha hemolysin | 1:400 | 0.055 | 6 |
| 3. Streptococcal Group B and type III antigen | 1:60 | 0.520 | 120 |

[a]Determined from chequer board antigen titrations. See tables
[b]Obtained by Kjeldahl Nitrogen determination
[c]Determined by Indole test

Titration of ELISA antigens

The results of the chequer board antigen titrations are shown in Table 4, (staphylococcal α hemolysin) Table 5, (staphylococcal somatic antigen), and Table 6, (streptococcal Group and type).

TABLE 4

Chequer board titration of staphylococcal α hemolysin to determine optimal concentration for ELISA[a]

| Antigen | Antiserum[b] | | | | |
|---|---|---|---|---|---|
|  | 1:10 | 1:20 | 1:40 | 1:80 | 1:160 |
| 1:8 | 2.110 | 1.703 | 1.411 | 1.036 | 0.878 |
| 1:116 | 1.976 | 1.614 | 1.326 | 1.029 | 0.787 |
| 1:32 | 2.079 | 1.706 | 1.422 | 1.118 | 0.876 |
| 1:64 | 2.165 | 1.334 | 1.474 | 1.075 | 0.829 |
| 1:128 | 1.926 | 1.665 | 1.481 | 1.063 | 0.789 |
| 1:256 | 1.895 | 1.670 | 1.462 | 1.067 | 0.830 |
| 1:512 | 1.828 | 1.647 | 1.419 | 1.053 | 0.795 |
| 1:800 | 1.974 | 1.650 | 1.291 | 0.963 | 0.741 |
| 1:1600 | 1.638 | 1.438 | 1.117 | 0.861 | 0.620 |
| 1:3200 | 1.463 | 1.170 | 0.887 | 0.739 | 0.472 |
| 1:6400 | 1.241 | 0.917 | 0.701 | 0.579 | 0.316 |
| 1:12800 | 1.043 | 0.810 | 0.587 | 0.400 | 0.281 |
| 1:25600 | 0.788 | 0.579 | 0.402 | 0.257 | 0.177 |

[a]Results expressed as absorbance values at 405 nm.
[b]Antiserum raised in rabbits against staphylococcal α hemolysin.

TABLE 5

Chequer board titration of staphylococcal somatic antigen to determine optimal concentration for ELISA[a]

| Antigen | Antiserum[b] | | | | |
|---|---|---|---|---|---|
|  | 1:10 | 1:20 | 1:40 | 1:80 | 1:160 |
| 1:4 | 2.680 | 2.680 | 2.681 | 2.051 | 1.403 |
| 1:8 | 2.680 | 2.680 | 2.681 | 2.042 | 1.161 |
| 1:16 | 2.680 | 2.680 | 2.681 | 1.925 | 1.056 |
| 1:32 | 2.680 | 2.680 | 2.681 | 1.849 | 1.083 |
| 1:64 | 2.680 | 2.680 | 2.681 | 1.758 | 1.068 |
| 1:128 | 2.680 | 2.680 | 2.543 | 1.676 | 0.920 |
| 1:256 | 2.681 | 2.680 | 2.291 | 1.546 | 0.853 |
| 1:512 | 2.681 | 2.671 | 1.782 | 1.260 | 0.751 |
| 1:1,024 | 2.328 | 2.035 | 1.439 | 0.922 | 0.682 |
| 1:2,048 | 1.764 | 1.538 | 0.980 | 0.655 | 0.779 |

[a]Results expressed as absorbance values at 405 nm.
[b]Antiserum raised in rabbits against *Staphylococcus aureus* strain 305 bacterin.

TABLE 6

Chequer board titration of Group B, type III streptococcal system to determine optimal concentrations for ELISA[a]

| Anti-streptococcal Igs[b] | Antigen | | | | | | | |
|---|---|---|---|---|---|---|---|---|
|  | Undiluted | 1:10 | 1:20 | 1:40 | 1:80 | 1:160 | 1:320 | 1:640 |
| 1:20 | 1.983 | 1.656 | 1.735 | 1.856 | 1.788 | 1.194 | 0.910 | 0.782 |
| 1:40 | 2.025 | 1.826 | 1.843 | 2.017 | 1.893 | 1.293 | 1.252 | 0.790 |
| 1:80 | 1.921 | 1.882 | 1.912 | 1.950 | 1.810 | 1.388 | 1.134 | 0.863 |
| 1:160 | 1.983 | 1.966 | 2.089 | 2.228 | 2.121 | 1.684 | 1.404 | 1.090 |
| 1:320 | 2.013 | 2.078 | 2.127 | 2.273 | 2.079 | 1.799 | 1.573 | 1.198 |

TABLE 6-continued

Chequer board titration of Group B, type III streptococcal system to determine optimal concentrations for ELISA[a]

| Anti-streptococcal Igs[b] | Antigen | | | | | | | |
|---|---|---|---|---|---|---|---|---|
| | Undiluted | 1:10 | 1:20 | 1:40 | 1:80 | 1:160 | 1:320 | 1:640 |
| 1:640 | 1.855 | 1.927 | 2.090 | 2.086 | 1.970 | 1.697 | 1.471 | 1.148 |
| 1:1280 | 1.692 | 1.786 | 1.917 | 1.883 | 1.855 | 1.299 | 1.120 | 0.401 |
| 1:2560 | 1.319 | 1.312 | 1.390 | 1.409 | 1.332 | 0.537 | 0.483 | — |
| 1:5120 | 0.850 | 0.483 | 0.553 | 0.639 | 0.560 | 0.313 | 0.373 | — |
| 1:10240 | 0.853 | 0.469 | 0.293 | 0.277 | 0.425 | 0.140 | 0.189 | — |

[a]Results expressed as absorbance values at 405 nm.
[b]Antiserum raised in rabbits against Str. agalactiae type III. Igs precipitated using 35% saturated ammonium sulfate.
Antiserum raised in guidea pigs against Str. agalactiae type III used on all wells at a dilution of 1:50.

Absorbance values for the 2 staphylococcal antigens remained stable for each antiserum dilution until the antigen concentration became a limiting factor in the test system. In the case of the α hemolysin, this occurred following the 1:512 dilution and in the case of the somatic antigen, it occurred following the 1:64 dilution. Subsequently the α hemolysin preparation was used in tests at a dilution of 1:400 in $CO_3$ buffer and the somatic antigen was used at a dilution of 1:50 in $CO_3$ buffer.

The rabbit anti-streptococcal Igs showed an apparent "prozone phenomena" at high concentrations. This was evident at dilutions of 1:20 to 1:80 where absorbance values exhibited a tendency to increase. A plateau effect was seen from 1:160 through 1:640 for all the dilutions of the streptococcal extract antigen. Subsequently the absorbance values declined with increasing dilutions indicating that the anti-streptococcal Igs had become a limiting factor in the reaction. The Ig preparation was subsequently used in tests at a dilution of 1:300 in $CO_3$ buffer.

The concentration of the streptococcal antigen became a limiting factor in the test system at a dilution of 1:80 since the absorbance values decreased with further dilutions. The antigen was used in subsequent tests at a dilution of 1:50 in PBS-T.

Titration of Milk samples

Figures 1, 2, 3:
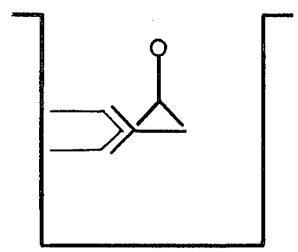
FIG. 3 graphically represents comparative ELISA values for IgG in milk specific for staphylococcal alpha hemolysin. Cows 1964 and 1902 subjected to staphylococcal bacterin-toxoid stimulation. Cow 2004 saline control. Milk samples were uniformly diluted 1:6 in PBS-T (Example FIG. 4 graphically represents comparative ELISA values for IgG in milk specific for staphylococcal alpha hemolysin. Cows 2022 and 2228 subjected to satphylococcal bacterin-toxoid stimulation. Cow 1635 saline control.
Figures 1, 2, 3, 4:
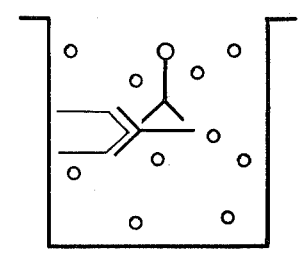
Figure 3:
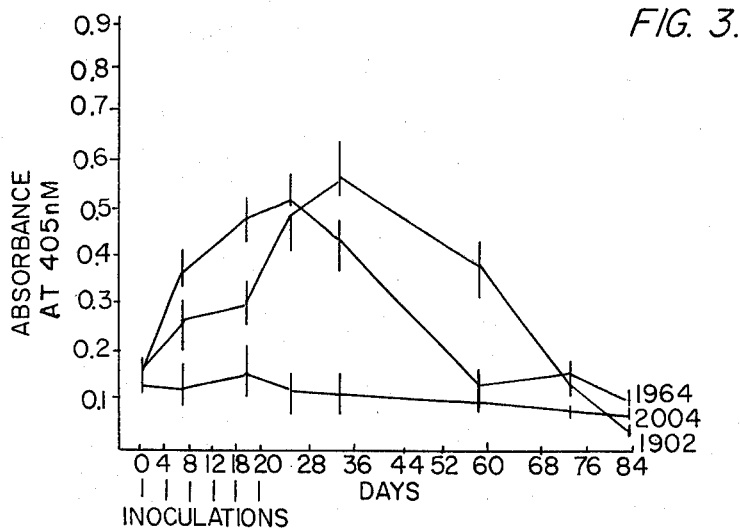
Figure 4:
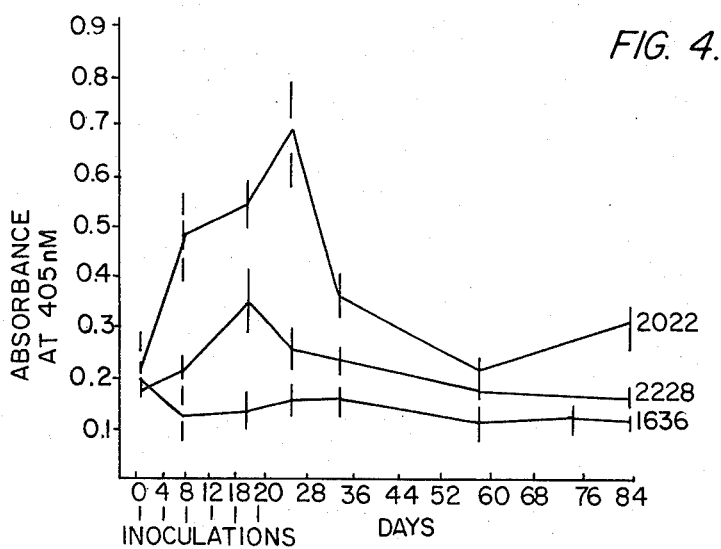
Figure 5:
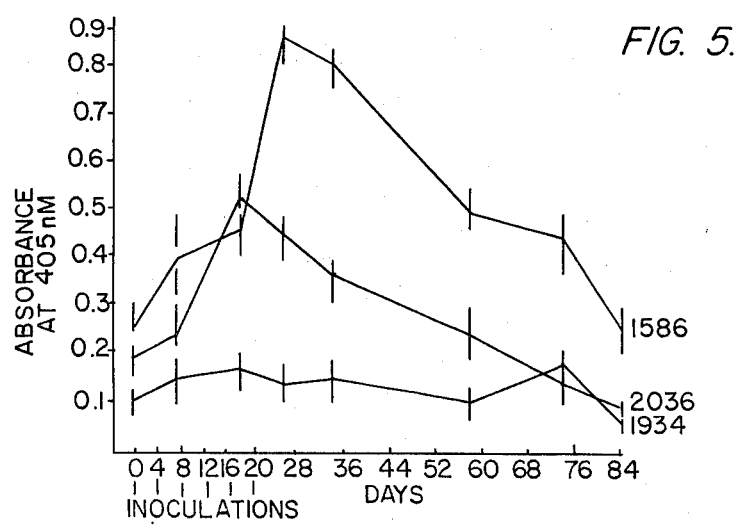
FIG. 5 graphically represents comparative ELISA values for IgG in milk specific for staphylococcal alpha hemolysin. Cow 1586 and cow 2936 subjected to satphylococcal bacterin-toxoid stimulation. Cow 1923 saline control.

The results of titration of positive milk samples when graphed as mean and standard error of absorbance values at 405 nm are linear. Therefore, a suitable dilution of 1:6 in PBS-T was selected for subsequent evaluation of milk samples. Immunization experiment Results of the ELISA's from the 9 cow immunization experiment are shown in FIGS. 3-5. Each milk sample was tested on 4 occasions and the results are expressed as the mean of the absorbance value at 405 nm±1 standard deviation. Using a standard staphylococcal α hemolysin preparation (Burroughs Wellcome, Greenville, NC) as described, an absorbance value of 1.0 at 405 nm obtained in an ELISA system was estimated to be equivalent to 0.06 I.U. of anti-α hemolysin activity per ml of milk.

Each of the 3 Figures show 2 animals which received inoculations of the antigenic preparation versus one control animal which received saline. Control animals (1934, 1635, and 2004) showed no significant variation in IgG specific for staphylococcal α hemolysin over the 84 day experimental period. The 6 inoculated animals showed a variable IgG response in terms of both the rate of development of the antibody response and the level attained. Peak levels were reached over the period of day 18 to day 34, cows number 2228, 3036 and cow number 1902 being the first and last to peak, respectively. The rate of antibody decline was also variable. By day 84, 64 days following the last inoculation, all cows had returned to preinoculation levels.

Discussion

Ninety percent of bovine mastitis is caused by the Gram positive cocci. It seems that a major component of the mammary glands defense against these pathogens is antibody mediated [Norcross, J.A.V.M.A., 170:1228-1231 (1977)]. Studies of the immune response of the gland with a view to immunization should, therefore, be geared towards analysis of the efficacy of various stimuli in the production of specific antibodies within the gland. In order to effectively assess various methods of immunization, a method of assay for Ig's is necessary which is sensitive, specific and discerns the relative contribution of each class to the response. ELISA fulfills these requirements and has been shown in this chapter to be adaptable for use as an assay of an immune response in the lactating mammary gland.

The ELISA was subsequently used to assay the immune responsiveness of the bovine gland following the administration of various preparations of antigens. The test was used as an indicator of humoral immune response.

EXAMPLE II

This Example relates to the effect of natural infection on antibody levels in milk specific for staphylococcal antigens.

INTRODUCTION $IgG_1$ is selectively transferred from the blood into lacteal secretions [Lascelles et al, "Localized humoral immunity with particular reference to ruminants", 1974, 170-208; Lascelles, 62:154-160(1979); Larson et al, J. Dairy Sci., 63:665-671 (1980)]. Under conditions of udder inflammation, this selective transfer mechanism probably no longer operates. The mammary barrier, when compromised by irritants, allows the passage of blood components into milk. Serum albumin, sodium chloride, sodium bicarbonate, neutrophil leucocytes and immunoglobulins increase in milk as a result of the inflammatory process [McDowell et al, Aust.Vet.Jour. 50:533-536 (1974); Larson et al, J.Dairy Sci., 63:665-671 (1980); Schalm, J.A.V.M.A. 170:1137-1140(1977)].

It has been shown that 0.01 ug of endotoxin per quarter is sufficient to cause the outpouring of leucocytes into a gland whereas 0.1 to 1.0 ug per quarter is necessary to cause the appearance of serum IgG, IgM and complement in milk [Reiter et al, Report, National Institute for Research in Dairying, p. 61 (1968)]. In addition, the concentration of Ig in milk increases relatively slowly following insult. Mackenzie et al using 135I labelled 7S γ globulin showed that the maximum concentrations of Igs was not attained until 24 hours after insult of the glands of ewes by *S. aureus* [McDowell et al, supra.].

An experiment was carried out to evaluate the specificity of the Ig response in infected cows with respect to the infecting pathogen, the purpose being to determine if antibody was present in the mammary gland as a result of existing and/or prior infection.

MATERIALS AND METHODS

Animals

A herd of 42 lactating Holstein Friesian and Jersey cows with a previous history of mastitis caused by *S. aureus and Str. agalactiae* were selected for evaluation.

Sampling procedure

Milk samples were collected aseptically from all 4 quarters of each cow prior to evening miling, on 2 occasions with a 2 day interval.

Microbiological culture

Approximately 0.2 ml of each quarter sample was plated on an esculin bovine blood agar plate and incubated at 37° C. for 24 hours. Microbiological identification was based on colony morphology, hemolytic pattern, Gram stain and where relevant, the CAMP test and tube coagulase test [Microbiological procedures for the diagnosis of bovine mastitis, National Mastitis Council, Washington, D.C., University of New Hampshire Press (1969)]. Milk samples were subsequently processed and stored for ELISA as described herein.

Cytological evaluation

Somatic cell counts were carried out by means of the Coulter counter using the method preserbed by the International Dairy Federation [Tolle, Inter. Dairy Fed. Boll. Pt. II (1967)].

Serotyping

All isolates of *Str. agalactiae* were subjected to immunological typing by means of Ouchterlony microimmunodiffusion method [Ouchterlony, Prg.Allergy, 5:1 (1958); Wilkinson, Preparation of Group B Streptococcus typing antisera (personal communication)]. The method was modified by the addition of 3% polyethylene glycol (w/v) to the gels [Harrington et al, *Immunochem.*, 8:413-421 (1971)].

Phage typing

All isolates of *S. aureus* were subjected to phage typing using the international set of bovine phages, and the method prescribed by the international Association of Microbiological Societies [Blair et al, *W.H.O. Bull.* 214:771-784, (1961)]. The phages used were: 119, 84, 52A, 116, 76, 107, 118, 6, 42E, 72, 102, 53, 117, 29 and 3A. All isolates of *S. aureus* were subjected to analysis of the phages at their respective routine test dilutions (RTD) and at 1000 RTD.

Preparation of antigens for ELISA

Staphylococcal α hemolysin was produced using *A. aureus* strain Wood 46. This strain was selected because it is a consistently high producer of α hemolysin [Slanetz, *Am.J.Vet.Res.*, 26:688-695 (1965)]. Production of α hemolysin was by the method of Coulter. Purification was carried out by extraction using 0.15 M sodium acetate [Coulter, *J. Bacteriol.*, 92:1655-1662 (1966)].

Staphylococcal somatic antigen was prepared from an *S. aureus* isolate cultured from a member of the herd, which was representative of the predominant phage type identified. The method of preparation was that described in Example I.

Streptococcal Group and type antigen was prepared from *Str. agalactiae* type III which was the type identified in the herd. The method of preparation was that described in Example I.

Titration of the 3 antigens for use in ELISA was carried out as described in EXAMPLE I.

Assay of milk antibody

The levels of IgG in milk specific for staphylococcal somatic antigen, α hemolysin and streptococcal Group B and type III antigen was assayed by means of ELISA. The ELISA procedure, using each of the respective antigens, was as described in Example I. All milk samples were subjected to duplicate analyses at a dilution of 1:6 in PBS-T.

RESULTS

Microbiological Culture and Somatic Cell Counts

Assessment of cytological-bacteriological findings was based on the guidelines established by the International Dairy Federation (IDF) in 1971 [Tolle, *Inter.-Dairy Fed.Bull.*, Pt.II(1967)].

TABLE 7

Evaluation of Cytological-Bacteriological Findings*

| Cell count | Pathogenic micro-organisms | |
|---|---|---|
| per ml milk | not isolated | isolated |
| <500,000 | normal secretion | latent infection |
| >500,000 | non-specific mastitis | mastitis |

*Table taken from: Tolle A. International Dairy Federation Annual Bulletin (1971). Part II. A monograph on bovine mastitis-Part I.

Cows were allocated on the basis of the above table to one of 5 groups. These were (1) Normal (12 animals), (2) Nonspecific mastitis and mastitis caused by pathogens other than *S. aureus* or *Str. agalactiae* (14 animals), (3) Mastitis caused by *S. aureus* (8 animals), (4) Mastitis caused by *Str. agalacetaie* (6 animals), (5) Mastitis caused by a combined infection with *S. aureus* and *Str. agalacetiae* (2 animals). Cows were distributed to their respective positive groups if either or both sample dates were classified positive. Animals were not stratified according to the number of quarters which were infected. Pathogens which were isolated from cows in group 2 included streptococci other than *Str. agalacetiae* and coagulase negative staphylococci.

A summary of the infection status of the herd is tabulated in Table 8. With the exception of group 1, all groups had average cell counts which were greater than the defined normal, i.e. $>500 \times 10^3$ cells/ml. The mean cell count of group 1 was $78 \times 10P \pm 9 \times 10^3$ cells/ml.

TABLE 8

Summary of Infection status of herd

| Infection Groups | Number of Quarters in Group | Culture Positive[a] | Culture and Cell Count Positive | Cell Count × 10³/ml, Group Mean ± S.E. |
|---|---|---|---|---|
| 1. Normal | 96 | — | — | 78 ± 9 |
| 2. Nonspecific and other pathogen mastitis | 110 | NA[b] | NA | 1165 ± 182 |
| 3. S. aureus mastitis | 64 | 40.6% | 30.48% | 930 ± 158 |
| 4. Str. agalactiae mastitis | 48 | 47.9% | 33.3% | 870 ± 231 |
| 5. S. aureus and Str. agalactiae mastitis | 16 | 18.8% S. aureus 68.8% Str. agalactiae | 12.5% S. aureus 56.3% Str. agalactiae | 1406 ± 306 |

[a]Culture positive for S. aureus and/or Str. agalactiae.
[b]Not applicable.

Serotyping

All isolates of Str. agalactiae were serotyped as type III.

Phage typing

Thirteen of the 18 representative S. aureus isolates at RTD and 16 at 1000 RTD typed positive with phage 119. Two isolates were, therefore, considered to be untypable.

ELISA Results

The mean absorbance value at 405 nm for each group, the standard error and the number of animals contained in the group are shown in Tables 9–11.

TABLE 9

Results of ELISA for IgG in milk specific for staphylococcal alpha hemolysin[a]

| Infection Groups | S1[b] Mean SE | S2 Mean SE | n[c] |
|---|---|---|---|
| 1. Normal | 0.345 0.050 | 0.233 0.033 | 12 |
| 2. Nonspecific & other pathogen mastitis | 0.414 0.102 | 0.304 0.059 | 14 |
| 3. S. aureus mastitis | 0.507 0.081 | 0.399 0.033 | 8 |
| 4. Str. agalactiae mastitis | 0.385 0.052 | 0.268 0.058 | 6 |
| 5. S. aureus & Str. agalactiae mastitis | 0.501 0.370 | 0.415 0.271 | 2 |

[a]Results expressed as absorbance at 405 nm.
[b]Sample. S1 and S2 taken with a 2 day interval.
[c]Number of cows per group.

TABLE 10

Results of ELISA for IgG in milk specific for streptococcal Group B, type III antigen[a]

| Infection Groups | S1[b] Mean SE | S2 Mean SE | n[c] |
|---|---|---|---|
| 1. Normal | 0.422 0.058 | 0.348 0.092 | 12 |
| 2. Nonspecific & other pathogen mastitis | 0.633 0.063 | 0.382 0.044 | 14 |
| 3. S. aureus mastitis | 0.618 0.101 | 0.336 0.025 | 8 |
| 4. Str. agalactiae mastitis | 0.738 0.125 | 0.426 0.081 | 6 |
| 5. S. aureus & Str. aglactiae mastitis | 0.821 0.010 | 0.603 0.015 | 2 |

[a]Results expressed as absorbance at 405 nm.
[b]Sample. S1 and S2 taken with a 2 day interval.
[c]Number of cows per group.

TABLE 11

Results of ELISA for IgG in milk specific for staphylococcal somatic antigen[a]

| Infection Groups | S1[b] Mean S.E. | S2 Mean S.E. | n[c] |
|---|---|---|---|
| 1. Normal | 0.674 0.108 | 0.402 0.044 | 12 |
| 2. Nonspecific and other pathogen mastitis | 0.775 0.158 | 0.720 0.122 | 14 |
| 3. S. aureus mastitis | 1.163 0.180 | 0.973 0.164 | 8 |
| 4. Str. agalactiae mastitis | 1.257 0.106 | 1.145 0.180 | 6 |
| 5. S. aureus and Str. agalactiae | 1.234 0.121 | 1.196 0.119 | 2 |

[a]Results expressed as absorbance at 405 nm.
[b]Sample. S1 and S2 taken with a 2 day interval.
[c]Number of cows per group.

Student tests were carried out to assess the presence of a statistically significant difference in antibody levels between Group 1 (normal cows) and the other groups for the 2 samples. The antibody levels specific for staphylococcal somatic antigen in groups 3, 4 and 5 differed from the antibody levels of group 1 at a 0.005 level of significance. Group 2 (nonspecific and other pathogen mastitis) did not differ significantly from the normal group.

Antibody levels specific for staphylococcal α hemolysin were significantly different only in group 3 which was infected with S. aureus (at a 0.02 level of significance).

Antibodies against streptococcal extract antigen were significantly different from the normal cows in the case of 2 groups—Str. agalactiae infected and combined S. aures-Str. agalactiae infected cows (groups 4 and 5, respectively). This difference was significant at a 0.025 level. It is pertinent to note that of the 16 quarters evaluated in group 5 animals, 12.5% of the quarters were infected with Str. agalactiae.

DISCUSSION

The results indicate that there is a significant elevation in the level of specific antibody in the milk of infected cows to antigens of the infecting organism. In the group where the cows are infected "nonspecifically" or with a heterologous organism, there is no statistically significant evidence that there is an increase in antibody specific for either staphylococcal or streptococcal antigens in spite of average cell counts which are well above normal, i.e. $1.165 \times 10^6$ cells/ml. The one exception to this is the group of cows which are infected with Str. agalactiae (group 4), since they show a significant reaction to the staphylococcal somatic antigen but not to the α hemolysin.

The data indicate that natural infection results in an increase in the level of specific antibody in milk; however, it is not possible to conclude from this experiment whether the antibody is local or humoral in origin.

It is interesting to note that the relative increase in the levels of specific antibody in the milk of a group of naturally infected cows although significant, is very low in comparison to the relative increase in vaccinated cows. To illustrate this point, groups of cows vaccinated under conditions described therein, showed a peak response to staphylococcal α hemolysin which was approximately 25 fold the level of antibody detectable in normal control cows. In the group of cows naturally infected with S. aureus with an average cell count of $9.3 \times 10^5$ cells/ml of milk, there sas a 1.5 fold increase over normal control cows with respect to the same antigen.

EXAMPLE III

This Example relates to the antibody response in milk following immunization with increasing concentrations of staphlococcal and streptococcal antigens.

INTRODUCTION

It seemed appropriate that a rationale for the usage of a particular vaccine system should be established prior to attempts to assess its protective efficacy. In the investigation of mastitis vaccines as reported in the literature, no reference has been made to a relative evaluation of the antigen mass used; vaccine dosages employed appear to have been chosen empirically. A dose response experiment was, therefore, carried out using S. aureus and Str. agalactiae antigens of known concentration. The humoral immune response of the lactating mammary gland to increasing concentrations of the relevant antigens was assessed by means of the ELISA.

MATERIALS AND METHODS

Vaccine Preparation

The S. aureus strain 305 bacterin and staphylococcal α hemolysin toxoid were produced and inactivated as described previously, Strain Wood 46 was used for production of the toxin.

Str. agalactiae type III was grown in Todd Hewitt broth (Difco Laboratories, Detroit, MI) which was modified according to Baker et al [Baker et al, J.Exper.Med, 143:158-270 (1976)]. The organisms were harvested by centrifugation at g and washed in sterile saline. Inactivation was by means of suspension in 0.3% formolized saline at 24° C. for 4 days. The inactivated organisms were washed twice in sterile saline and resuspended in the same dilutant. The concentration of the 3 antigen components for each group of cows is tabulated in Table 12. The vaccines were administered as a composite of the 3 antigen preparation.

TABLE 12

Concentration of S. aureus, Str. agalactiae bacterins and toxoid staphylococcal α hemolysin administered to each group of cows[a]

| Vaccine Group | Str. agalactiae | | S. aureus | | Staphylococcal α hemolysin |
|---|---|---|---|---|---|
| | CFU/ml | mg N/ml | CFU/ml | mg N/ml | mg N/ml |
| 1 | Saline | Saline | Saline | Saline | Saline |
| 2 | $1.4 \times 10^7$ | 0.08 | $6 \times 10^7$ | 0.13 | 0.005 |
| 3 | $1.3 \times 10^8$ | 0.88 | $6 \times 10^8$ | 1.37 | 0.05 |
| 4 | $5.6 \times 10^8$ | 3.50 | $2.4 \times 10^9$ | 5.48 | 0.1 |
| 5 | $2.24 \times 10^9$ | 14.0 | $9.6 \times 10^{10}$ | 21.9 | 0.2 |
| 6 | $8.9 \times 10^9$ | 56.3 | $3.8 \times 10^{10}$ | 87.6 | 0.4 |

[a]Concentrations of the antigens are expressed as colony forming units/ml (CFJ/ml) and total mg N/ml obtained by Kjeldahl Nitrogen determination [Kabat, "Experimental Immunochemistry", 2nd ed., 1961, p. 476-483. C.C. Thomas, Illinois, U.S.A.]

Animals

Fifty two lactating Holstein Friesian Cows were allocated randomly to 6 groups. There was no stratification of the animals on the basis of lactation stage, number, or previous history of mastitis. Cows which were dried off during the experimental period were excluded from data analysis.

Immunization procedure

A 5 ml dose of the relevant vaccine preparation was inoculated into the region of the right external inguinal lymph node using an 18 gauge 1½ inch needle. This was followed by a second inoculation in the region of the left lymph node, 21 days later.

Sampling procedure

Quarter milk samples were collected aseptically as described previously in Example I. Sampling was carried out on 2 occasions prior to the first vaccination (−6 and −8 days) and subsequently every 14 days.

Microbiological culture

Approximately 0.1 ml of each quarter sample was plated on an esculin-bovine blood-agar plate and incubated at 37° C. for 24 hours. Microbiological identification was based on the methods described by the National Mastitis Council ["Microbiological procedures for the diagnosis of bovine mastitis", National Mastitis Council, Washington, D.C., University of New Hampshire Press (1969)]. Following microbiological culture, samples were processed and stored for ELISA as described in Example I.

Assay of milk antibody

Each milk sample was tested in duplicate in an ELISA system against each of 3 antigens. The 3 antigens used were staphylococcal somatic antigen, staphylococcal α hemolysin and streptococcal Group B type III antigen, prepared as described in Example I. The milk was diluted 1:6 in PBS-T. Three-tenths of an ml of this dilution was tested in ELISA. The procedure for ELISA was as described in Example I.

RESULTS

Microbiological culture

S. aureus was not isolated from any milk sample during the course of the experiment. Animals which cultured positive for Str. agalactiae were excluded from the assessment of antibody levels specific for this bacteria on that sample date. Other bacteria which were isolated from the herd included *Streptococcus* species, *Corynebacterium bovis*, staphylococcus species. These isolates were not considered in relation to data processing unless the infected animals showed evidence of clinical mastitis. Cows developing clinical signs were excluded from data evaluation.

ELISA results

The pseficic IgG responses of the groups of animals to each of the 3 antigens are set forth in Tables 13, 14 and 15. The tabulated results include in addition to the mean absorbance values, the standard error of the mean and the number of animals contributing to that sample's data.

TABLE 13

Results of ELISA for quantitation of IgG in milk specific for staphylococcal alpha hemolysin[a]

| Vaccine Group | $-1$[b] | $+2$ | $+4$ | $+6$ | $+8$ | $+10$ | $+12$ | $+14$ | $+17$ |
|---|---|---|---|---|---|---|---|---|---|
| 1: | | | | | | | | | |
| $\bar{x}$ | 0.211 | 0.243 | 0.208 | 0.365 | 0.310 | 0.331 | 0.210 | 0.180 | 0.125 |
| S.E. | 0.041 | 0.013 | 0.029 | 0.029 | 0.036 | 0.033 | 0.030 | 0.025 | 0.028 |
| n | 11 | 6 | 6 | 6 | 6 | 6 | 6 | 5 | 5 |
| 2: | | | | | | | | | |
| $\bar{x}$ | 0.217 | 0.548 | 0.483 | 0.487 | 0.419 | 0.372 | 0.284 | 0.283 | 0.236 |
| S.E. | 0.020 | 0.105 | 0.128 | 0.116 | 0.059 | 0.059 | 0.044 | 0.054 | 0.052 |
| n | 14 | 7 | 7 | 7 | 7 | 7 | 7 | 7 | 7 |
| 3: | | | | | | | | | |
| $\bar{x}$ | 0.311 | 0.668 | 0.664 | 0.739 | 0.526 | 0.509 | 0.342 | 0.254 | 0.148 |
| S.E. | 0.040 | 0.100 | 0.060 | 0.059 | 0.060 | 0.058 | 0.060 | 0.051 | 0.046 |
| n | 16 | 7 | 8 | 7 | 7 | 7 | 7 | 5 | 5 |
| 4: | | | | | | | | | |
| $\bar{x}$ | 0.243 | 0.718 | 0.854 | 0.749 | 0.592 | 0.492 | 0.331 | 0.304 | 0.223 |
| S.E. | 0.027 | 0.073 | 0.129 | 0.069 | 0.044 | 0.052 | 0.031 | 0.043 | 0.059 |
| n | 20 | 10 | 9 | 10 | 10 | 10 | 10 | 10 | 10 |
| 5: | | | | | | | | | |
| $\bar{x}$ | 0.235 | 0.868 | 1.011 | 0.978 | 0.798 | 0.598 | 0.413 | 0.428 | 0.177 |
| S.E. | 0.023 | 0.070 | 0.104 | 0.113 | 0.056 | 0.046 | 0.043 | 0.053 | .030 |
| n | 13 | 7 | 7 | 7 | 7 | 6 | 6 | 5 | 5 |
| 6: | | | | | | | | | |
| $\bar{x}$ | 0.167 | 0.939 | 1.054 | 0.884 | 0.719 | 0.563 | 0.326 | 0.301 | 0.180 |
| S.E. | 0.048 | 0.095 | 0.056 | 0.085 | 0.083 | 0.091 | 0.053 | 0.042 | 0.043 |
| n | 10 | 6 | 6 | 6 | 6 | 6 | 5 | 5 | 5 |

[a]Results are expressed as absorbance at 405 nm. Vaccine was administered at time 0 and +3.
[b]Values for the preinoculation sample at time −1 are the mean of 2 samples per cow taken at 8 and 6 days prior to vaccination at time 0.

TABLE 14

Results of ELISA for quantitation of IgG in milk specific for staphylococcal somatic antigen[a]

| Vaccine Group | $-1$[b] | $+2$ | $+4$ | $+6$ | $+8$ | $+10$ | $+12$ | $+14$ | $+17$ |
|---|---|---|---|---|---|---|---|---|---|
| 1: | | | | | | | | | |
| $\bar{x}$ | 0.231 | 0.308 | 0.174 | 0.328 | 0.347 | 0.308 | 0.307 | 0.266 | 0.198 |
| S.E. | 0.024 | 0.021 | 0.024 | 0.036 | 0.022 | 0.036 | 0.035 | 0.045 | 0.018 |
| n | 11 | 6 | 6 | 6 | 6 | 6 | 6 | 5 | 5 |
| 2: | | | | | | | | | |
| $\bar{x}$ | 0.262 | 0.392 | 0.497 | 0.374 | 0.345 | 0.422 | 0.408 | 0.376 | 0.259 |
| S.E. | 0.018 | 0.038 | 0.075 | 0.058 | 0.035 | 0.060 | 0.045 | 0.057 | 0.021 |
| n | 14 | 7 | 7 | 7 | 7 | 7 | 7 | 7 | 7 |
| 3: | | | | | | | | | |
| $\bar{x}$ | 0.345 | 0.621 | 0.679 | 0.535 | 0.475 | 0.511 | 0.454 | 0.373 | 0.309 |
| S.E. | 0.027 | 0.073 | 0.073 | 0.036 | 0.045 | 0.081 | 0.045 | 0.050 | 0.036 |
| n | 16 | 8 | 8 | 7 | 7 | 7 | 7 | 7 | 5 |
| 4: | | | | | | | | | |
| $\bar{x}$ | 0.250 | 0.573 | 0.746 | 0.544 | 0.467 | 0.438 | 0.434 | 0.377 | 0.333 |
| S.E. | 0.027 | 0.063 | 0.083 | 0.050 | 0.033 | 0.027 | 0.021 | 0.036 | 0.044 |
| n | 20 | 10 | 9 | 10 | 10 | 10 | 10 | 10 | 10 |

TABLE 14-continued

Results of ELISA for quantitation of IgG in milk specific for staphylococcal somatic antigen[a]

| Vaccine Group | $-1$[b] | $+2$ | $+4$ | $+6$ | $+8$ | $+10$ | $+12$ | $+14$ | $+17$ |
|---|---|---|---|---|---|---|---|---|---|
| 5: | | | | | | | | | |
| $\bar{x}$ | 0.287 | 0.739 | 1.042 | 0.828 | 0.678 | 0.570 | 0.581 | 0.440 | 0.323 |
| S.E. | 0.022 | 0.080 | 0.071 | 0.089 | 0.051 | 0.050 | 0.065 | 0.048 | 0.041 |
| n | 13 | 7 | 7 | 7 | 7 | 6 | 6 | 5 | 5 |
| 6: | | | | | | | | | |
| $\bar{x}$ | 0.257 | 0.718 | 1.005 | 0.702 | 0.663 | 0.505 | 0.464 | 0.444 | 0.277 |
| S.E. | 0.024 | 0.063 | 0.098 | 0.111 | 0.066 | 0.072 | 0.044 | 0.037 | 0.021 |
| n | 10 | 6 | 6 | 6 | 6 | 6 | 6 | 5 | 5 |

[a]Results are expressed as absorbance at 405 nm. Vaccine was administered at time 0 and +3.
[b]Values for the preinoculation sample at time −1 are the mean of 2 samples per cow taken at 8 and 6 days prior to vaccination at time 0.

TABLE 15

Results of ELISA for quantitation of IgG in milk specific for streptococcal antigen[a]

| Vaccine Group | $-1$[b] | $+2$ | $+4$ | $+6$ | $+8$ | $+10$ | $+12$ | $+14$ | $+17$ |
|---|---|---|---|---|---|---|---|---|---|
| 1: | | | | | | | | | |
| $\bar{x}$ | 0.357 | 0.313 | 0.419 | 0.551 | 0.420 | 0.384 | 0.319 | 0.425 | 0.349 |
| S.E. | 0.030 | 0.035 | 0.060 | 0.054 | 0.058 | 0.039 | 0.035 | 0.037 | 0.036 |
| n | 12 | 6 | 6 | 6 | 6 | 6 | 6 | 5 | 5 |
| 2: | | | | | | | | | |
| $\bar{x}$ | 0.468 | 0.573 | 0.509 | 0.795 | 0.618 | 0.557 | 0.472 | 0.395 | 0.378 |
| S.E. | 0.046 | 0.076 | 0.037 | 0.062 | 0.066 | 0.065 | 0.065 | 0.040 | 0.036 |
| n | 15 | 7 | 7 | 7 | 7 | 6 | 7 | 7 | 7 |
| 3: | | | | | | | | | |
| $\bar{x}$ | 0.512 | 0.540 | 0.598 | 0.922 | 0.612 | 0.526 | 0.489 | 0.342 | 0.458 |
| S.E. | 0.045 | 0.095 | 0.058 | 0.063 | 0.119 | 0.064 | 0.063 | 0.068 | 0.110 |
| n | 13 | 7 | 7 | 6 | 6 | 6 | 6 | 4 | 5 |
| 4: | | | | | | | | | |
| $\bar{x}$ | 0.536 | 0.537 | 0.911 | 1.301 | 0.885 | 0.730 | 0.608 | 0.578 | 0.399 |
| S.E. | 0.052 | 0.050 | 0.078 | 0.085 | 0.078 | 0.062 | 0.070 | 0.099 | 0.033 |
| n | 18 | 9 | 8 | 9 | 9 | 9 | 9 | 7 | 8 |
| 5: | | | | | | | | | |
| $\bar{x}$ | 0.516 | 0.659 | 1.335 | 1.727 | 1.153 | 0.916 | 0.807 | 0.871 | 0.583 |
| S.E. | 0.060 | 0.062 | 0.108 | 0.185 | 0.093 | 0.136 | 0.142 | 0.216 | 0.093 |
| n | 12 | 6 | 6 | 6 | 6 | 6 | 6 | 5 | 5 |
| 6: | | | | | | | | | |
| $\bar{x}$ | 0.569 | 0.685 | 1.334 | 1.686 | 1.240 | 0.971 | 0.693 | 0.757 | 0.680 |
| S.E. | 0.037 | 0.048 | 0.143 | 0.185 | 0.162 | 0.125 | 0.049 | 0.073 | 0.075 |
| n | 10 | 6 | 6 | 6 | 6 | 6 | 5 | 5 | 5 |

[a]Results are expressed as absorbance at 405 nm. Vaccine was administered at time 0 and +3.
[b]Values for the preinoculation sample at time −1 are the mean of 2 samples per cow taken at 8 and 6 days prior to vaccination at time 0.

Pre-inoculation levels at −1 week are expressed as the mean of 2 samples taken with a 2 day interval. These values are extrapolated as straight lines until inoculation takes place at time 0. On each of the 3 graphs a reference line is included which arbitrarily represents a division of the response into positive (above the line) and negative (below the line). Group 1, which received saline, did not vary significantly in antibody levels throughout the experiment with respect to all 3 ELISA antigens.

The specific IgG response in milk to staphylococcal somatic antigen is shown in Table 14. The sample taken 2 weeks after the first inoculation already showed significant increases in the milk antibody levels of groups 3 through 6. Peak responses occurred 4 weeks after the first inoculation. From the peak levels at 4 weeks, there was a steady decline of antibody levels in all groups. By 12 to 14 weeks, groups 2 through 4 again became negative using the reference line as a basis for comparison.

By the same criteria, at 14 to 17 weeks, groups 5 and 6 also returned to a negative status. Statistical analysis of the peak response at 4 weeks by means of the student t test indicated that there was no significant statistical difference between Groups 5 and 6, but that Group 5 differed from Group 4 at the 0.02 level of significance.

The specific IgG response in milk to staphylococcal alpha hemolysin is shown in Table 13. The sample, taken 2 weeks after the first inoculation, showed significant increase in the levels of antibody of all vaccinated groups. Peak responses occurred at 4 weeks in Groups 4 through 6. Groups 2 and 3 peak at 2 and 6 weeks, rspectively. Although the peak levels were maintained for a longer time than in the case of the somatic antigen (approximately 4 weeks), the rate of antibody decline after the 6th week was such that by weeks 10 to 12, all groups except for 5 had returned to negative levels. By weeks 14 to 17, all groups had fallen below the reference line. Statistical analysis of the peak response at 4 weeks by means of the student t test indicated that the difference between Groups 4, 5 and 6 was not statistically significant, but that Group 3 differed from Group 5 at the 0.02 level of significance.

The specific IgG response in milk to streptococcal Group B type III antigen is shown in Table 15. Vaccine groups 5 and 6 were the only 2 groups to have increased above the reference line by week 2 of the experiment. By week 4, Groups 4 and 6 showed significant increases in antibody levels. The lower dose levels of Groups 2 and 3 seemed to require a second inoculation (week 3) before an antibody response was seen at week 6. The peak levels of all groups occurred 6 weeks after the first inoculation. By week 8, Groups 2 and 3 were again negative. By week 12, Group 4 was negative and by week 17, Group 5 was also. Group 6 was still marginally above the positive-negative value line at week 17.

Statistical analysis of the peak response at 6 weeks by means of the student t test indicated that there was no significant difference between Groups 5 and 6 but that Group 5 differed from Group 4 at the 0.05 level of significance.

DISCUSSION

From the results obtained in this experiment, it would seem that the optimum concentration of these antigens to use is that which was administered to Group 5 vaccinates. That is: $9.6 \times 10^{10}$ CFU/ml of *S. aureus* (21.9 mg N/ml), $2.24 \times 10^9$ CFU/ml of *Str. agalactiae* (14 mg N/ml) and 0.1 mg N/ml of toxoided staphylococcal α hemolysin preparation.

It appears that relatively large increments in dosage are required in order to cause a discernible difference in antibody levels. It is possible that there is a range of antigenic mass within the limits of which there is no differential effect on the antibody level. This is supported by the 3 ranges, represented, respectively, by (a) Group 2, (b) Groups 3 and 4, and (c) Groups 5 and 6. It is conceivable, therefore, that further increases in antigen mass would result in further elevations in antibody levels.

A feature emerging from this experiment is the relatively prolonged latent period prior to the occurrence of an antibody response following vaccination with *Str. agalactiae* when compared with the latent period for the *S. aureus* or toxoid preparations. In addition, in the case of *Str. agalactiae* doses administered to Groups 2 and 3 evidently necessitated a second inoculation in order to give a detectable response. Finally, the response to *Str. agalactiae* is significantly more transient in general than the response to the other 2 antigens. A probable explanation for this discrepancy is found in the fact that the capsule of *Str. agalactiae* as a polysaccharide is a relatively weak immunogen [Slanetz et al, *Am. J. Vet. Res.*, 26: 688–695 (1965)].

Although by week 17 essentially all groups are below the arbitrary positive-negative line, it is notable that the vaccinated groups still showed a discernible antibody difference which is reflective of the dosage administered.

It is interesting to note the bacterial numbers which have been used in previous work on mastitis vaccines. Brock et al believed it unlikely that mastitis vaccination would work on the basis of results obtained using an extremely low dose *S. aureus* bacteria [Brock et al, Res.Vet. Sci., 19:152–158 (1975)]. More optimistic reports were made by workers using high dose vaccines. [McDowell and Watson McDowell et al, Aust.Vet. Jour. 50:533–536 (1974)] and Blobel and Berman [Blobel et al, *Amer.J.Vet.Res.*, 23:92 (1962)] used high dose *S. aureus* vaccines containing $1.5 \times 10^9$ and $2 \times 10^9$ cells per ml, respectively, in conjunction with intensive inoculation regimes. Thier affirmative results are not necessarily evidence of the efficacy of high dosage vaccines since many other differentials were involved in these experiments. However, it seems rational to conclude that the use of the correct antigens at a dosage level which is proven to elicit an immune response in the lactating gland is more likely to give positive results than a vaccine causing no detectable response in the target organ.

EXAMPLE IV

This Example relates to the immunogenic properties and cross reactivity of *S. aureus, Str. agalactiae* and staphylococcal α hemolysin, administered separately and in combination.

INTRODUCTION

It has been demonstrated that peptidoglycan extracts of certain Gram positive bacterial cell walls function as immunopotentiators [Kotani et al, *Biken J.*, 18:77–92 (1975)]. This has been shown to be true of both *S. aureus* [Kotani et al, *Biken J.*, 18:93–103 (1975); Kotani et al, *Biken J.*, 18:77–92 (1975)] and of many Streptococcus species [Kotani et al, *Biken J.*, 18:77–92 (1975)]. The effect of the whole cell wall on the immune response is less than that of the extracted peptidoglycan. This immunopotentiation is manifested by an increase in both immunoglobulin production and cell mediated immunity [Stewart-Tull, D.E. S., *Ann.Rev.Microbial.*, 34:311–340 (1980)]. In addition, *Bordetella pertussis* has been shown to exert significant adjuvant effects on the humoral immune response when administered concurrently with a variety of antigens including other bacteria, soluble proteins, and heterologous RBC's [Finger, *4th Int.Convoc.Immunol.*, 132–166 (1974)].

It has also been demonstrated that microorganisms belonging to different genera may exhibit an immunologic cross reactivity [Berman et al, *Proc. 60th Ann.Meeting U.S. Livestock Sanitary Assoc.*, p. 97–103 (1957); Hurvell, *Ada.Vet.Scand.*, 13:472–438 (1972); Prince et al, J.Comp.Pathol.Therap., 76:315–320].

The vaccines used to date in this project have been a composite containing a variety of antigens of the two bacteria, *S. aureus* and *Str. agalactiae*. The questions raised, therefore, were whether certain components of the vaccine may have acted as immunopotentiators and whether immunological cross reactivity occurred between the antigens administered.

In order to establish the possibility of either phenomena occurring, an experiment was carried out to compare the immunogenic properties and cross reactivity of each of the vaccine components when administered separately and in combination.

MATERIALS AND METHODS

Vaccine preparation

*S. aureus* strain 305, *Str. agalactiae* type III and staphylococcal α hemolysin were produced and inactivated as described previously. The components and concentration of the vaccines administered to each group of cows are shown in Table 16.

TABLE 16

Components and concentration of *S. aureus*, Str. agalactiae bacterins and toxoided staphylococcal α hemolysin administered to each group of cows.

| Vaccine Group | Antigen Components | Antigen Concentration CFU/ml[a] | mg N/ml[b] |
|---|---|---|---|
| 1 | Saline | — | — |
| 2 | S. aureus | $9.6 \times 10^{10}$ | 21.9 |
|   | Str. agalactiae | $2.24 \times 10^9$ | 14.0 |
|   | Staphylococcal α hemolysin | — | 0.2 |
| 3 | S. aureus | $9.6 \times 10^{10}$ | 21.9 |
| 4 | Str. agalactiae | $2.24 \times 10^9$ | 14.0 |
| 5 | Staphylococcal α hemolysin | — | 0.2 |

[a]Colony forming units per ml.
[b]Obtained by means of Kjeldahl nitrogen determination [Kabat, "Experimental Immunochemistry", 2nd Ed., 1961 p. 476, C.C. Thomas, Illinois]

Animals

Forty three lactating Holstein Friesian cows were randomly allocated to 5 groups. There was no stratification on the basis of a lactation stage, number or previous history of mastitis. Samples taken from cows 14 days or less, prior to drying off, were excluded from data analysis.

Immunization procedure

Each group of animals was vaccinated as described in Example III with 5 mls of the appropriate inoculum.

Sampling procedure and microbiological culture

There were carried out as described in Example III.

Assay of milk antibodies

Each milk sample was tested in duplicate in an ELISA system against each of 3 antigens. The 3 antigens were staphylococcal somatic antigen and α hemolysin and streptococcal Group B, type iii antigen prepared as described in Example I. The ELISA method was that described in Example I, with two modifications. Milk samples were incubated for 60 minutes as opposed to 40 minutes in previous tests. A reference milk sample was included 4 times in each test. The substrate reaction was read when the average absorbance of the 11 reference samples reached a predetermined value [Voller et al, "The enzyme linked immunosorbent assay (ELISA)", Dynatech Europe, Borough House, Rue du Pre, Guernsey, G.B. (1979)].

RESULTS

Microbiological culture

*S. aureus* and *Str. agalactiae* were not isolated from any milk sample during the experiment. Staphylococcus species other than *S. aureus*, Streptococcus species other *Str. agalactiae*, and coliform species were isolated during the experiment. These isolates were not considered in analysis of the data. Cows which developed clinical mastitis, irrespective of aetiology, were excluded from data evaluation for the sample data prior to and following the clinical period.

ELISA results

The specific IgG responses of each group of animals to each of the 3 antigens are shown in Tables 17-19. The results are expressed as mean absorbance values at 405 nm for that group. The standard error of the mean and the number of animals contributing to that samples data are also included.

The results of the response to each of the 3 antigens was also graphically suited.

The specific IgG responses in milk to staphylococcal somatic antigen are shown in Table 17. Group 2, representing the cows which received the 3 antigens as a composite vaccine, shows the typical response illustrated in Example III. Group 3 which received the *S. aureus* bacterin alone showed a response which was similar to but slightly lower than that of Group 2. This difference was not statistically significant for any of the sample dates as assessed by a student t test. The remaining groups, 4 and 5, which were inoculated with *Str. agalactiae* bacterin and staphylococcal α hemolysin, respectively, showed no significant deviations from the levels of antibody of the saline control animals.

The specific IgG responses in milk to staphylococcal α hemolysin are shown in Table 18. Group 2 again showed a typical response which was significantly greater than the reactions of Groups 3, 4 and 5. Groups 3 and 4, which received *S. aureus* bacterin and *Str. agalactiae*, respectively, showed a fluctuating response with no clearly defined pattern. Group 5 which was inoculated with staphylococcal α hemolysin showed a typical response pattern. The peak of this response, however, was less than the peaks attained by groups 3 and 4.

The specific IgG responses in milk to streptococcal Group B, type III antigen are shown in Table 19. Groups 2 and 4 which received the combined vaccine and the *Str. agalactiae* bacterin, respectively, showed a typical response and did not differ significantly from each other in this response. The other groups, 3 and 5, which received *S. aureus* bacterin and α hemolysin, respectively, did not deviate significantly from the levels of the antibody of the saline control group.

TABLE 17

Results of ELISA for quantitation of IgG in milk specific for staphylococcal somatic antigen[a]

| Vaccine Group | | Sample Time (Weeks) | | | | | | |
|---|---|---|---|---|---|---|---|---|
| | | −1 | +2 | +4 | +6 | +8 | +10 | +14 |
| 1: | x̄ | 0.261 | 0.348 | 0.224 | 0.194 | 0.192 | 0.192 | 0.240 |
| | S.E. | 0.025 | 0.054 | 0.032 | 0.032 | 0.020 | 0.014 | 0.035 |
| | n | 9 | 9 | 8 | 7 | 6 | 6 | 6 |
| 2: | x̄ | 0.228 | 0.706 | 0.589 | 0.530 | 0.447 | 0.389 | 0.317 |
| | S.E. | 0.037 | 0.054 | 0.080 | 0.084 | 0.074 | 0.095 | 0.057 |
| | n | 8 | 9 | 9 | 9 | 8 | 8 | 8 |
| 3: | x̄ | 0.236 | 0.657 | 0.527 | 0.353 | 0.359 | 0.312 | 0.282 |

TABLE 17-continued
Results of ELISA for quantitation of IgG in milk specific for staphylococcal somatic antigen[a]

| Vaccine Group | | −1 | +2 | +4 | +6 | +8 | +10 | +14 |
|---|---|---|---|---|---|---|---|---|
| | S.E. | 0.029 | 0.077 | 0.105 | 0.054 | 0.082 | 0.068 | 0.039 |
| | n | 8 | 8 | 7 | 6 | 6 | 6 | 6 |
| 4: | $\bar{x}$ | 0.295 | 0.360 | 0.243 | 0.251 | 0.259 | 0.225 | 0.221 |
| | S.E. | 0.087 | 0.085 | 0.055 | 0.056 | 0.053 | 0.053 | 0.044 |
| | n | 7 | 8 | 8 | 8 | 8 | 7 | 7 |
| 5: | $\bar{x}$ | 0.278 | 0.352 | 0.211 | 0.220 | 0.247 | 0.197 | 0.235 |
| | S.E. | 0.049 | 0.043 | 0.033 | 0.037 | 0.050 | 0.030 | 0.059 |
| | n | 8 | 9 | 9 | 9 | 7 | 7 | 7 |

[a]Results are expressed as absorbance at 405 nm. Vaccine was administered at time 0 and +3.

TABLE 18
Results of ELISA for quantitation of IgG in milk specific for staphylococcal α hemolysin[a]

| Vaccine Group | | −1 | +2 | +4 | +6 | +8 | +10 | +14 |
|---|---|---|---|---|---|---|---|---|
| 1: | $\bar{x}$ | 0.198 | 0.185 | 0.164 | 0.179 | 0.091 | 0.126 | 0.100 |
| | S.E. | 0.031 | 0.035 | 0.039 | 0.034 | 0.015 | 0.018 | 0.011 |
| | n | 9 | 9 | 8 | 7 | 6 | 6 | 6 |
| 2: | $\bar{x}$ | 0.162 | 0.515 | 0.517 | 0.469 | 0.257 | 0.263 | 0.154 |
| | S.E. | 0.027 | 0.062 | 0.083 | 0.072 | 0.066 | 0.023 | 0.019 |
| | n | 8 | 9 | 9 | 9 | 8 | 7 | 8 |
| 3: | $\bar{x}$ | 0.226 | 0.287 | 0.299 | 0.261 | 0.164 | 0.255 | 0.130 |
| | S.E. | 0.057 | 0.040 | 0.026 | 0.034 | 0.033 | 0.055 | 0.020 |
| | n | 8 | 7 | 7 | 6 | 6 | 6 | 6 |
| 4: | $\bar{x}$ | 0.218 | 0.272 | 0.217 | 0.285 | 0.169 | 0.235 | 0.146 |
| | S.E. | 0.064 | 0.039 | 0.061 | 0.072 | 0.033 | 0.048 | 0.030 |
| | n | 7 | 8 | 8 | 8 | 8 | 7 | 7 |
| 5: | $\bar{x}$ | 0.197 | 0.259 | 0.154 | 0.234 | 0.122 | 0.159 | 0.116 |
| | S.E. | 0.014 | 0.075 | 0.043 | 0.041 | 0.015 | 0.026 | 0.009 |
| | n | 8 | 9 | 9 | 9 | 7 | 7 | 7 |

[a]Results are expressed as absorbance at 405 nm. Vaccine was administered at time 0 and +3.

TABLE 19
Results of ELISA for quantitation of IgG in milk specific for streptococcal Group B type III antigen[a]

| Vaccine Group | | −1 | +2 | +4 | +6 | +8 | +10 | +14 |
|---|---|---|---|---|---|---|---|---|
| 1: | $\bar{x}$ | 0.748 | 0.619 | 0.498 | 0.512 | 0.521 | 0.469 | 0.476 |
| | S.E. | 0.088 | 0.062 | 0.060 | 0.061 | 0.056 | 0.043 | 0.083 |
| | n | 9 | 9 | 8 | 7 | 6 | 6 | 6 |
| 2: | $\bar{x}$ | 0.533 | 1.096 | 2.244 | 1.731 | 1.381 | 1.139 | 0.787 |
| | S.E. | 0.045 | 0.087 | 0.168 | 0.121 | 0.103 | 0.127 | 0.083 |
| | n | 8 | 9 | 9 | 9 | 8 | 7 | 8 |
| 3: | $\bar{x}$ | 0.595 | 0.683 | 0.622 | 0.481 | 0.493 | 0.454 | 0.439 |
| | S.E. | 0.074 | 0.091 | 0.105 | 0.057 | 0.062 | 0.047 | 0.050 |
| | n | 8 | 8 | 7 | 6 | 6 | 6 | 6 |
| 4: | $\bar{x}$ | 0.677 | 1.077 | 2.095 | 1.590 | 1.243 | 1.011 | 0.641 |
| | S.E. | 0.093 | 0.065 | 0.163 | 0.172 | 0.083 | 0.117 | 0.038 |
| | n | 7 | 8 | 8 | 8 | 8 | 7 | 6 |
| 5: | $\bar{x}$ | 0.766 | 0.672 | 0.590 | 0.575 | 0.576 | 0.557 | 0.456 |
| | S.E. | 0.124 | 0.064 | 0.092 | 0.052 | 0.062 | 0.107 | 0.052 |
| | n | 8 | 9 | 9 | 9 | 7 | 7 | 7 |

[a]Results are expressed as absorbance at 405 nm. Vaccine was administered at time 0 and +3.

DISCUSSION

The specific IgG response to streptococcal Group B type III antigen and staphylococcal somatic antigen shows that there is no evidence of either cross reactivity or immunopotentiation between S. aureus and Str. agalactiae with respect to these antigens. In the case of response to staphylococcal somatic antigen, the cows which received the combined vaccine showed a reaction which was slightly greater than that of the cows receiving S. aureus alone. This difference was not statistically significant as assessed by a student t test. The difference may be a function of reaction to the hemolysin component of the vaccine since the cows in group 2 received toxoid. Staphylococcal somatic antigen as prepared for use in the ELISA should contain only low levels of α hemolysin since somewhat less than 1% is associated with the cell [Wiseman, Bacteriol.Rev., 39:317–344 (1975)]. α hemolysin has been identified on the membrane of disrupted staphylococci [Coulter et al, Infect. Immun., 4:650–655 (1971)], and it is possible that this specificity accounts for the slightly elevated response of the Group 2 cows.

The specific IgG response to staphylococcal α hemolysin indicates that it is probably necessary to use a combination vaccine in order to stimulate a response to the α hemolysin. The response to the combined vaccine is significantly greater than the fluctuating reaction seen following inoculation with either of the 3 components alone.

It is concluded from these experiments that either bacteria (S. aureus or Str. agalactiae) administered alone will ilicit a response to itself as efficiently as when the bacteria are administered in combination, with no evidence of immunological cross reaction occurring. In the case of the α hemolysin preparation, it appears that it is necessary to administer the toxoid in conjunction with a bacterin to elicit an optimum response.

EXAMPLE V

This Example relates to the effect of selected adjuvants on the response of the mammary gland to a staphylococcal and streptococcal antigen.

INTRODUCTION

The results obtained in the dose response experiments described in Example III show that it is possible to stimulate a significant antibody response in milk. The duration of this response, however, is relatively transient. By 14 to 17 weeks after inoculation, the antibody level has essentially returned to pre-inoculation values in cows which received optimal dosages of staphylococcal and streptococcal antigens. This period represents approximately half of an average lactation cycle. It was considered that the most potentially efficient means of maintaining antibody levels throughout a lactation was by the use of immunopotentiating agents.

Shean and Overcast examined the effects of several adjuvants on the immunogenic properties of a staphylococcal mastitis vaccine in cows. Assay of response was by quantitation of serum anti-α hemolysin. The preparations considered were Freunds complete and incomplete adjuvant, alum and sodium alginate. Freunds complete adjuvant elicited a response which was significantly higher than vaccine alone. The other adjuvants showed no improvement over vaccine alone [Skean et al, "Efficacy of staphylococcal vaccines to elicit antistaphylococcal alpha hemolysin in diary cows"]. Watson and Lascelles compared Freunds incomplete adjuvant to vaccine alone. Assay of antibody by means of bacterial agglutination showed that serum and whey titres were substantially higher in the cows which received adjuvant in addition to the vaccine [Watson & Lascelles, Res. Vet. Sci., 18:182–185 (1975)].

Several other immunopotentiators have been used in conjunction with mastitis vaccines on a noncomparative basis. These include Freunds complete adjuvant [Brock et al, *Res. Vet. Sci.,* 19:152–158 (1975)] and aluminum hydroxide gel [Slanetz et al, *Am.J.Vet.Res.,* 26:688–695 (1965)].

An experiment was carried out in order to evaluate the effects of various adjuvants on the response of the lactating gland to a stimulus, as measured by the ELISA. The aim being to select the adjuvant which was most efficacious in elevating the level of the response and extending its duration. The preparations which were examined included Freunds incomplete adjuvant "Handbook of experimental immunology", Weir (ed.), 3rd ed. Blackwell Scientific Publications, Oxford p.A3.1–A3.15; Herbert et al, Internatl.Symp. on Adjuvants of Immunity, Utrecht; *Symp.Series Immunobiol.Standard,* 6:213–220, Karger, Basel(1967)], *Bordetella pertussis* (B. pertussis) [Finger, *4th Int.Convoc.* Immunol., Buffalo NY 1974, p 132–166, Karger, Basel 1975], aluminum hydroxide gel [Hepple, Inter.-Symp.on Adjuv.of Immun., Utrecht; Symp. Series Immunobiol.Standard, 6:173–180, Karger, Basel (1967)] and a metabolizable lipid emulsion [Reynolds et al, *Amer.Soc.Microbial.,* 79th Ann. Meet. (1979)]. Freunds complete adjuvant was not considered because it does not constitute a practically feasible means of immunopotentiation in the bovine.

MATERIALS AND METHODS

Vaccine preparation

The vaccine was prepared as described in Example II. The concentration of antigens in the vaccine was $1.82 \times 10^{11}$ CFU/ml of *S. aureus* (43.8 mg N/ml), $4.48 \times 10^9$ CFU/ml of *Str. agalactiae* (28 mg N/ml), and 0.4 mg N/ml of toxoided staphylococcal α hemolysin. Equal volumes of this preparation and sterile saline were mixed for adminstration to animals in Groups 2 and 6. These were cows receiving vaccine alone and vaccine with *B. pertussis*, respectively.

Inclusion of adjuvant preparations in vaccine

Mineral oil.

A water-in-oil emulsion was prepared using equal volumes of vaccine and Freunds incomplete adjuvant (Difco Laboratories, Detroit MI) by means of a syringe method ["Handbook of experimental immunology", Weir (ed.), 3rd ed., Blackwell Scientific Publications, Oxford P.A3.1–A.3.15].

Aluminum hydroxide gel

The vaccine was adsorbed with equal volumes of a 2% aluminum hydroxide gel (Rehsorptar gel, Reheis Chemical Co., Chicago, IL).

Metabolizable lipid emulsion

Peanut oil (Standard Brands, Inc., New York, NY) glycerol (Mallinckrodt Inc., Paris, KY) and soybean lecithin (Natural Sales Co., Pittsburgh, PA) were mixed in relative proportions of 10:10:1 respectively [Reynolds et al, *Amer.Soc.Microbial.,* 79th Ann. Meet (1979)]. The preparation was sterilized by autoclaving. An emulsion was made using equal volumes of the adjuvant preparation and vaccine.

*Bordella pertussis*

*B. pertussis* was grown at 37° C. for 5 days on Bordet gengou agar plates (Difco Lab., Detroit, MI), enriched with 15% defibrinated rabbit blood. The organisms were harvested by washing of plates with sterile saline and inactivated by suspension in saline containing 1:10,000 Merthiolate Thimerosal (Eli Lilly and Co., Indianapolis, Ind) [Verway et al, Jour. Bact. 58:127–134 (1949)]. Following 3 washes in merthiolated saline the bacterial were resuspended to a final concentration of $4 \times 10^{10}$ cells/ml in sterile saline.

Animals

Fifty four lactating Holstein Friesan cows were randomly allocated to 5 groups in the same manner as described hereinbove. The groups of animals were vaccinated as follows: Group 1, Saline; Group 2, Vaccine; Group 3, Vaccine and aluminum hydroxide gel; Group 4, Vaccine and lipid emulsion; Group 5, Vaccine and mineral oil; and Group 6, Vaccine and *B. pertussis*. Samples taken from cows 14 days or less, prior to drying off, were excluded from data analysis.

Immunization procedure

Five ml of the relevant vaccine preparation was administered to each group of animals, on 2 occasions with a 21 day interval as described in Example III. Animals in Group 6 received 10 ml of the *B. pertussis* preparation, subcutaneously in the region of the semimembranosus and semitendinosus muscles, administered concurrent with the vaccine.

Sampling procedure
Microbiological culture

These were carried out as described in Example I.

Assay of milk antibody

The levels of IgG in milk specific for staphylococcal somatic antigen, α hemolysin and streptococcal Group B and type III antigen were assayed by means of ELISA. The ELISA procedure, using each of the respective antigens, was as described in Example I. All milk samples were subjected to duplicate analyses at a dilution of 1:6 in PBS-T.

RESULTS

Microbiological culture

*S. aureus* and *Str. agalactiae* were not isolated from any milk sample during the course of the experiment. Other bacteria which were isolated from the herd included Streptococcus species, Staphylococcus species and coliform species. These isolates were not considered in relation to data processing unless the infected animals showed evidence of clinical mastitis. Cows which developed clinical mastitis, irrespective of actiology, were excluded from data evaluation for the sample data prior to and following the clinical period.

ELISA results

Figure 6:
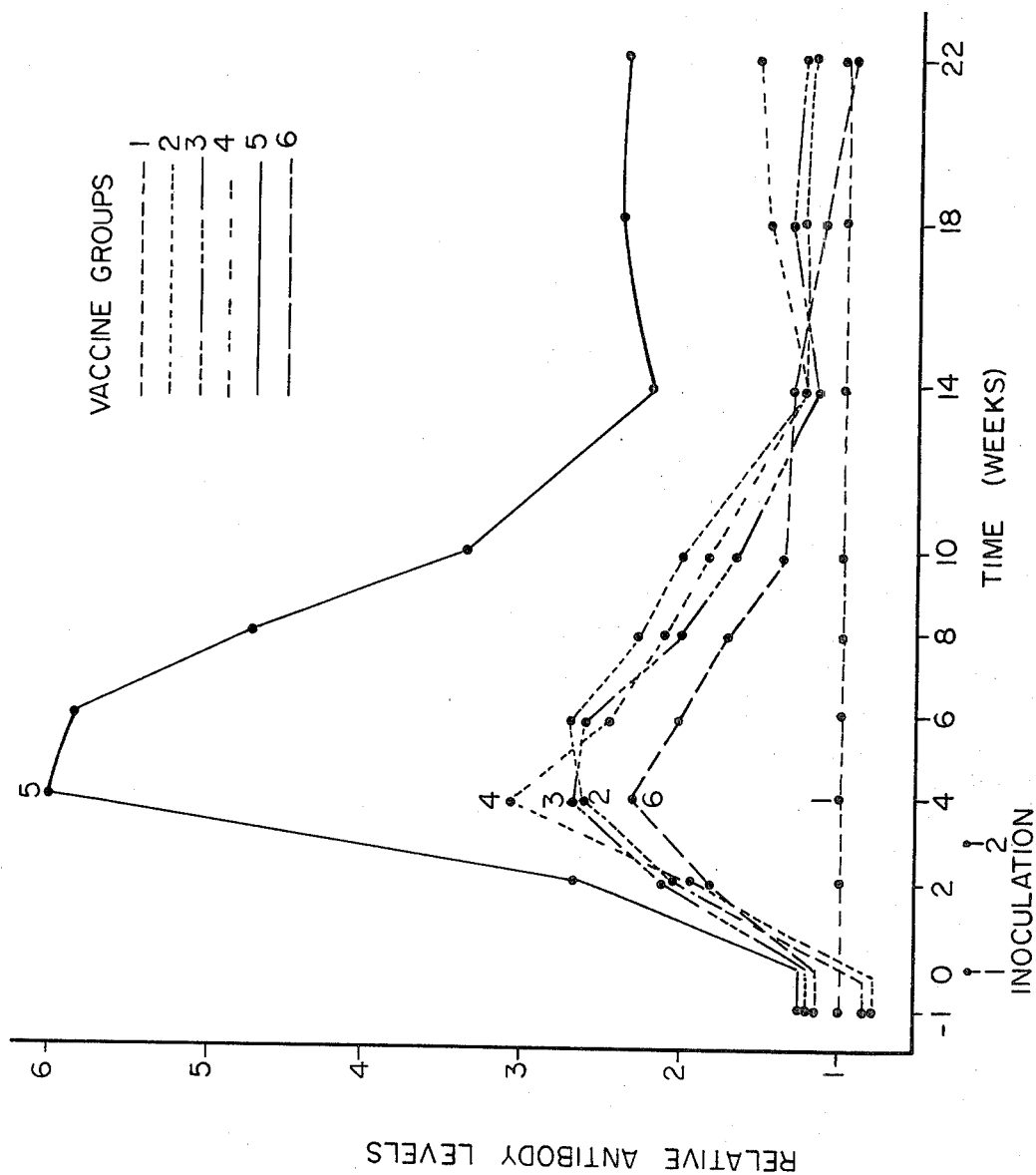
FIGS. 6 and 7 graphically represent the specific IgG responses in milk to the streptococcal somatic antigen and alpha hemolysin as set forth in Tables 20 and 21, respectively (Example V)
Figure 7:
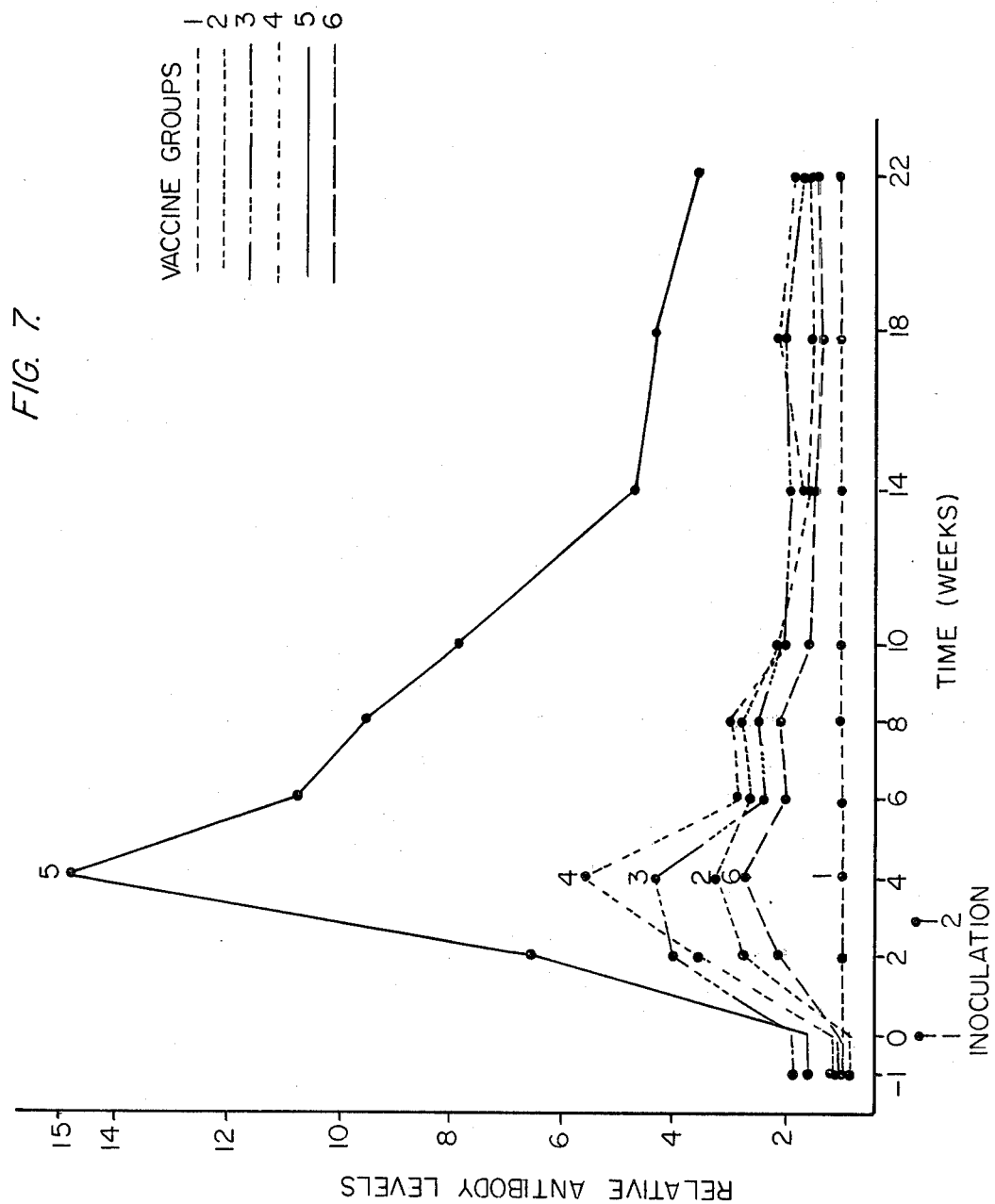
Figure 8:
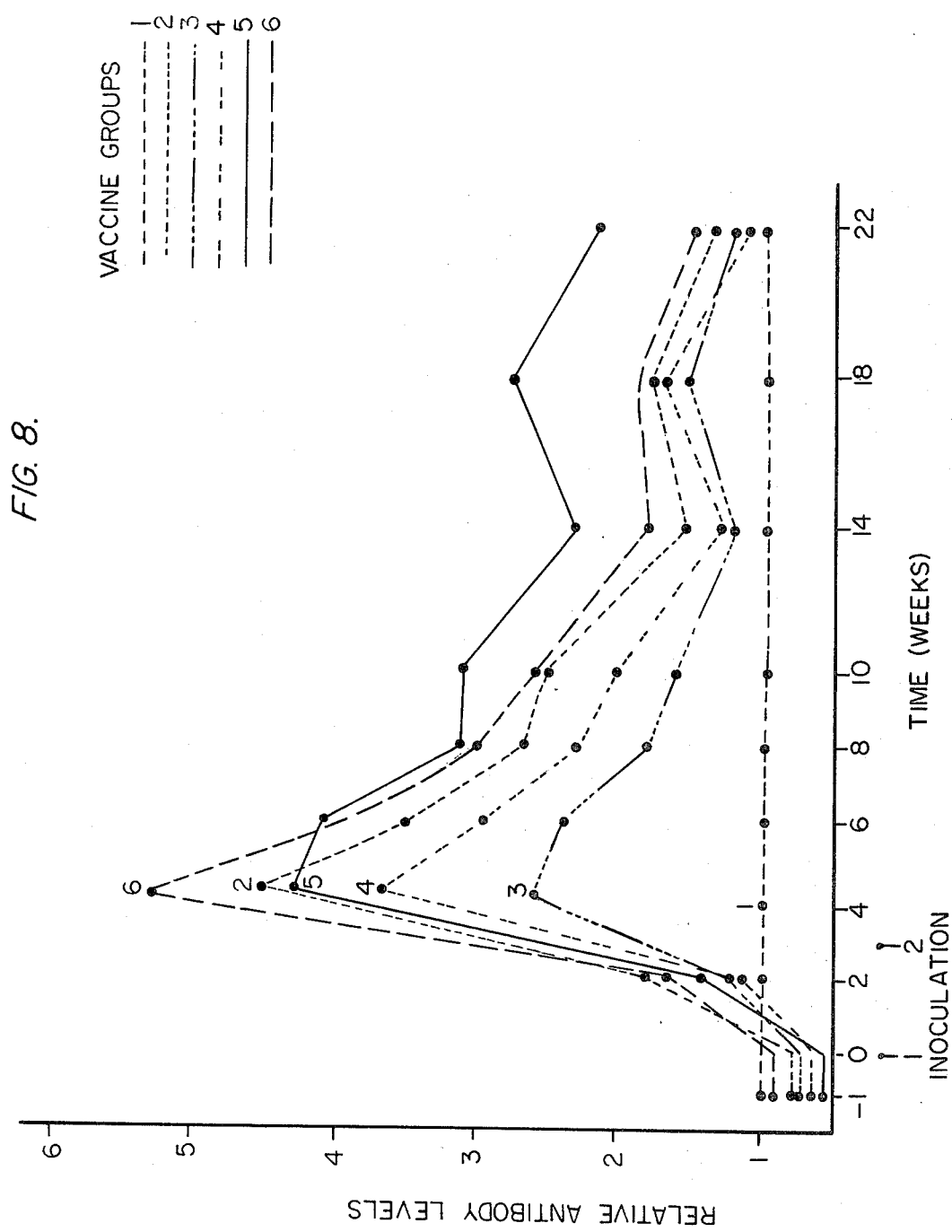
FIG. 8 graphically represents the specific IgG responses in milk to the streptococcal extract antigen as set forth in Table 22 (Example V).

The specific IgG responses of each group of animals to each of the 3 antigens are shown in Tables 20–22. The results are expressed as mean absorbance values at 405 nm for that group. The standard error of the mean and the number of animals contributing to that sample's data are also included. The specific IgG responses to staphylococcal somatic antigen and α hemolysin are shown in Tables 20 and 21 and FIGS. 6 and 7, respectively. The only adjuvant which exerted a significant effect in terms of level and duration of the response to the 2 antigens was mineral oil. Peak response in Group 5 cows to the staphylococcal somatic antigen showed a 6 fold increase over the antibody level of the saline control cows as opposed to a 2.7 fold increase shown by the animals which received vaccine alone. In the response to α hemolysin, this was a 14.8 fold and 3.2 fold increase, respectively. By 10 to 14 weeks post vaccination, the antibody levels of all groups of cows except those which received mineral oil adjuvant were approaching the levels of the control group. At this time, Group 5 still showed an antibody level which in the case of the α hemolysin was still comparable to the peak response of the other groups of cows which occurred at weeks 4 to 6. The levels of antisomatic antigen antibodies in the milk of Group 6 cows at this time was still 2.2 times the levels of the saline control groups. Specific antibodies in the milk of Group 5 cows to both of the staphylococcal antigens were still detectable at 22 weeks post vaccination. The specific IgG responses in milk to the streptococcal extract antigen are shown in Table 22 and FIG. 8. The height of the response did not appear to be affected in a statistically significant level by the inclusion of any of the adjuvant preparations. The duration of the response was extended somewhat by the inclusion of mineral oil in the vaccine. Group 5 still showed significantly different antibody levels at weeks 18 to 22 post vaccination, while the other groups of animals returned to approximate control levels by weeks 14 to 18 post vaccination.

TABLE 20

Results of ELISA for quantitation of IgG in milk specific for staphylococcal somatic antigen[a]

| Vaccine Group | Sample Time (Weeks) | | | | | | | | |
|---|---|---|---|---|---|---|---|---|---|
| | −1 | +2 | +4 | +6 | +8 | +10 | +14 | +18 | +22 |
| 1: | | | | | | | | | |
| $\bar{x}$ | 0.261 | 0.238 | 0.224 | 0.194 | 0.192 | 0.192 | 0.240 | 0.207 | 0.232 |
| S.E. | 0.025 | 0.054 | 0.032 | 0.032 | 0.020 | 0.014 | 0.035 | 0.037 | 0.040 |
| n | 9 | 9 | 8 | 7 | 6 | 6 | 6 | 5 | 5 |
| 2: | | | | | | | | | |
| $\bar{x}$ | 0.228 | 0.706 | 0.589 | 0.530 | 0.447 | 0.389 | 0.303 | 0.262 | 0.275 |
| S.E. | 0.037 | 0.054 | 0.080 | 0.084 | 0.074 | 0.095 | 0.064 | 0.046 | 0.048 |
| n | 8 | 9 | 9 | 9 | 8 | 8 | 7 | 7 | 7 |
| 3: | | | | | | | | | |
| $\bar{x}$ | 0.317 | 0.721 | 0.605 | 0.520 | 0.396 | 0.320 | 0.279 | 0.265 | 0.284 |
| S.E. | 0.053 | 0.082 | 0.055 | 0.066 | 0.061 | 0.027 | 0.029 | 0.033 | 0.049 |
| n | 9 | 9 | 9 | 9 | 9 | 9 | 9 | 8 | 7 |
| 4: | | | | | | | | | |
| $\bar{x}$ | 0.217 | 0.662 | 0.680 | 0.477 | 0.400 | 0.355 | 0.283 | 0.310 | 0.367 |
| S.E. | 0.022 | 0.061 | 0.065 | 0.041 | 0.037 | 0.051 | 0.031 | 0.048 | 0.089 |
| n | 9 | 9 | 9 | 9 | 9 | 9 | 9 | 8 | 8 |
| 5: | | | | | | | | | |
| $\bar{x}$ | 0.329 | 0.924 | 1.344 | 1.126 | 0.902 | 0.638 | 0.515 | 0.498 | 0.553 |
| S.E. | 0.043 | 0.075 | 0.138 | 0.107 | 0.073 | 0.059 | 0.043 | 0.067 | 0.087 |
| n | 8 | 9 | 9 | 9 | 9 | 9 | 9 | 9 | 9 |
| 6: | | | | | | | | | |
| $\bar{x}$ | 0.272 | 0.638 | 0.508 | 0.390 | 0.331 | 0.255 | 0.304 | 0.235 | 0.224 |
| S.E. | 0.032 | 0.075 | 0.053 | 0.047 | 0.044 | 0.038 | 0.052 | 0.030 | 0.022 |
| n | 9 | 8 | 8 | 8 | 7 | 7 | 7 | 5 | 5 |

[a]Results are expressed as absorbance at 405 nm. Vaccine administered at time 0 and +3.

TABLE 21

Results of ELISA for quantitation of IgG in milk specific for staphylococcal alpha hemolysin[a]

| Vaccine Group | Sample Time (Weeks) | | | | | | | | |
|---|---|---|---|---|---|---|---|---|---|
| | −1 | +2 | +4 | +6 | +8 | +10 | +14 | +18 | +22 |
| 1: | | | | | | | | | |
| $\bar{x}$ | 0.198 | 0.185 | 0.164 | 0.179 | 0.091 | 0.126 | 0.100 | 0.096 | 0.111 |
| S.E. | 0.031 | 0.035 | 0.039 | 0.034 | 0.015 | 0.018 | 0.011 | 0.017 | 0.017 |
| n | 9 | 9 | 8 | 7 | 6 | 6 | 6 | 5 | 5 |
| 2: | | | | | | | | | |
| $\bar{x}$ | 0.162 | 0.515 | 0.527 | 0.469 | 0.257 | 0.252 | 0.144 | 0.138 | 0.165 |
| S.E. | 0.027 | 0.062 | 0.083 | 0.072 | 0.066 | 0.023 | 0.018 | 0.024 | 0.019 |
| n | 8 | 9 | 9 | 9 | 8 | 6 | 7 | 7 | 7 |
| 3: | | | | | | | | | |
| $\bar{x}$ | 0.364 | 0.738 | 0.708 | 0.421 | 0.256 | 0.262 | 0.189 | 0.191 | 0.193 |
| S.E. | 0.079 | 0.105 | 0.079 | 0.059 | 0.020 | 0.023 | 0.018 | 0.017 | 0.044 |
| n | 9 | 9 | 9 | 9 | 9 | 9 | 9 | 8 | 7 |
| 4: | | | | | | | | | |
| $\bar{x}$ | 0.231 | 0.557 | 0.919 | 0.479 | 0.267 | 0.251 | 0.158 | 0.211 | 0.199 |
| S.E. | 0.029 | 0.072 | 0.093 | 0.038 | 0.033 | 0.029 | 0.018 | 0.020 | 0.030 |
| n | 9 | 9 | 9 | 9 | 9 | 9 | 9 | 8 | 8 |
| 5: | | | | | | | | | |
| $\bar{x}$ | 0.307 | 1.199 | 2.431 | 1.804 | 0.862 | 0.992 | 0.462 | 0.414 | 0.392 |
| S.E. | 0.054 | 0.204 | 0.099 | 0.161 | 0.096 | 0.092 | 0.036 | 0.047 | 0.064 |
| n | 9 | 9 | 9 | 9 | 9 | 9 | 9 | 9 | 9 |
| 6: | | | | | | | | | |
| $\bar{x}$ | 0.179 | 0.386 | 0.453 | 0.352 | 0.192 | 0.195 | 0.150 | 0.129 | 0.163 |
| S.E. | 0.028 | 0.051 | 0.065 | 0.056 | 0.030 | 0.023 | 0.025 | 0.021 | 0.018 |
| n | 9 | 8 | 8 | 8 | 7 | 7 | 7 | 5 | 5 |

[a]Results are expressed as absorbance at 405 nm. Vaccine administered at time 0 and +3.

TABLE 22

Results of ELISA for quantitation of IgG in milk specific for streptococcal Group B, type III antigen[a]

| Vaccine Group | Sample Time (Weeks) | | | | | | | | |
|---|---|---|---|---|---|---|---|---|---|
| | −1 | +2 | +4 | +6 | +8 | +10 | +14 | +18 | +22 |
| 1: | | | | | | | | | |
| $\bar{x}$ | 0.748 | 0.619 | 0.498 | 0.512 | 0.521 | 0.469 | 0.476 | 0.325 | 0.465 |
| S.E. | 0.088 | 0.062 | 0.060 | 0.061 | 0.056 | 0.043 | 0.083 | 0.047 | 0.061 |
| n | 9 | 9 | 8 | 7 | 6 | 6 | 6 | 5 | 5 |
| 2: | | | | | | | | | |
| $\bar{x}$ | 0.533 | 1.096 | 2.244 | 1.731 | 1.381 | 1.139 | 0.720 | 0.591 | 0.708 |
| S.E. | 0.045 | 0.087 | 0.168 | 0.121 | 0.103 | 0.127 | 0.056 | 0.049 | 0.064 |
| n | 8 | 9 | 9 | 9 | 8 | 7 | 7 | 7 | 7 |
| 3: | | | | | | | | | |
| $\bar{x}$ | 0.527 | 0.758 | 1.306 | 1.228 | 0.931 | 0.765 | 0.608 | 0.495 | 0.578 |
| S.E. | 0.079 | 0.063 | 0.060 | 0.088 | 0.075 | 0.056 | 0.072 | 0.032 | 0.053 |
| n | 9 | 9 | 9 | 9 | 9 | 9 | 9 | 8 | 7 |
| 4: | | | | | | | | | |
| $\bar{x}$ | 0.453 | 0.678 | 0.827 | 1.524 | 1.195 | 0.966 | 0.507 | 0.576 | 0.567 |
| S.E. | 0.051 | 0.048 | 0.123 | 0.083 | 0.090 | 0.075 | 0.053 | 0.051 | 0.076 |
| n | 9 | 9 | 9 | 9 | 9 | 9 | 9 | 8 | 8 |
| 5: | | | | | | | | | |
| $\bar{x}$ | 0.429 | 0.891 | 2.159 | 2.111 | 1.624 | 1.486 | 1.093 | 0.904 | 0.908 |
| S.E. | 0.033 | 0.077 | 0.148 | 0.161 | 0.134 | 0.105 | 0.088 | 0.076 | 0.124 |
| n | 8 | 9 | 9 | 9 | 9 | 9 | 9 | 9 | 9 |
| 6: | | | | | | | | | |
| $\bar{x}$ | 0.678 | 1.021 | 2.636 | 2.009 | 1.528 | 1.200 | 0.843 | 0.614 | 0.642 |
| S.E. | 0.052 | 0.086 | 0.043 | 0.151 | 0.122 | 0.096 | 0.119 | 0.101 | 0.051 |
| n | 9 | 8 | 8 | 8 | 7 | 7 | 7 | 5 | 5 |

[a]Results are expressed as absorbance at 405 nm. Vaccine administered at time 0 and +3.

DISCUSSION

Under the conditions of vaccination described, the adjuvant of choice is mineral oil. The inclusion of this adjuvant with staphylococcal antigens has a highly significant effect on the height and duration of the immune response following stimulation. The effects of the mineral oil on the response to the streptococcal antigens is less clearly affirmative although there is evidence of an extension of the duration of the response. This phenomenon is possibly attributable to the fact that the group and type antigens of Str. agalactiae are carbohydrate and are, therefore, less antigenic than the protein antigens of the staphylococci. It is possible that a higher dosage of *Str. agalactiae* in association with the mineral oil may elicit a heightened response. The dose response experiment described in Example II evaluated the response to vaccine alone. It may be that this dosage is not the optimum when the antigen is incorporated into an adjuvant.

A final point is the fact that the cows in Group 6 which received *B. pertussis* as an adjuvant were relatively poor responders with respect to the 2 staphylococcal antigens. However, in the case of the response to the streptococcal antigen, the peak attained by this group was the maximum response for all the groups, exceeding even that shown by Group 5 (mineral oil) animals. The mechanism of action of *B. pertussis* is such that an extension of the duration of the response is not necessarily expected [Finger, 4th Int.Concov. Immunol, Baffalo, NY 1974, p. 132–166, Karger, Basel 1975]. It is conceivable that *B. pertussis*, with further investigation of the variables involved, may prove to be the most efficacious immunopotentiator for *Str. agalactiae* bacterins.

EXAMPLE IV

This Example relates to the relative contribution of each immunoglobulin class and subclass to the immune response.

INTRODUCTION

The normal lactating mammary gland of the cow has little potential for the production of IgA and IgM [Butler et al, J.Immunol., 109:38–46 (1972); Watson, *Aus.J-.Biol.Sci.*, 33: 403–522 (1980)]. Local immunization prepartum results in increased secretion of both these Igs during the ensuing lactation [Wilson et al, *Immunol*, 23:313–320 (1972); Huber et al, Milchwissenssenshaft, 33:1–6 & 101–105 (1978); Wilson, Immunol., 23:947–955 (1972)]. It has also been demonstrated that systemic immunization using a bacterial antigen in adjuvant during mammary involution results in elevated levels of specific IgA and IgM in mil, but has little effect on IgG production [Watson et al, *Res.in Vet.Sci.*, 18:182–185 (1975)].

Immunization during lactation must of necessity be a systemic stimulus. The advantages of systemic over local stimulation are evident at a practical level. However, the lack of success encountered following a systemic stimulus has led to statements such as "antigenic stimulation at the local level is clearly the major (if not the only) factor influencing an immune response in the mammary glands of ruminants" [Watson, *Aus.J.Biol.-Sci.*, 33:403–522 (1980)]. The response following local stimulation is almost entirely IgA and IgM.

It is evident from an evaluation of the umoral immune response of the mamary gland and the mechanisms involved in antibacterial defense that it may be essential to stimulate the production of all classes and subclasses of specific antibody. $IgG_1$, the major secretory Ig in the bovine species, plays a major role in protection against extracellulary replicating bacteria. This Ig is almost entirely humoral in origin and local stimulation is expected to have little effect on a specific response within this class. Previous examples analyzed the immune response of the lactating gland in terms of IgG levels. This Example is concerned with analysis of this response to determine the relative contribution, if any, of IgA and IgM and in addition to clarify the IgG subclasses which are involved in the response.

MATERIALS AND METHODS

Animals

Twenty six lactating Holstein Friesian cows were randomly allocated to 3 groups. There was no stratification of the animals on the basis of lactation stage, number or previous history of mastitis. Animals which were dried off during the experiment were discarded from data analysis 14 days prior to drying off.

Vaccine preparation and immunization procedure

Animals were immunized with one of 3 preaprations. Group 1 received saline, Group 2 vaccine suspended in saline and Group 3 vaccine emulsified in Freunds incomplete adjuvant. The concentration, folume of the vaccine, and method for administration was as described for Groups 1, 2, and 5, respectively, in Example V.

Sampling procedure, Microbiological culture

These were carried out as described in Example I. Samples were taken 1 week prior to the first inoculation which was administered at time 0 and subsequently at week 4, week 8 and week 18.

Assay of milk antibody

Antibodies in milk with specificity for staphylococcal α hemolysin were assayed by means of a modified indirect ELISA. The procedure was as described in Example I, with one modification which allowed for concurrent determination of the relative contribution of each Ig class to the response. Following incubation of the milk samples, rabbit anti-bovine serum, monospecific for bovine IgA, IgM, $IgG_1$ and $IgG_2$ was added, at an appropriate dilution predetermined by titration and incubated at 37° C. for 40 minutes. The 4 antisera used were rabbit anti-bovine $IgG_1$ and $IgG_2$ (Miles Research Products Division, Box 2000, Elkhart, IN) and rabbit anti-bovine IgA and IgM (Pel-Freeze Biologicals, Box 68, Rogers, AR). All milk samples, diluted 1:6 in PBS-T were tested in duplicate, using each of the 4 monospecific antisera described above. Following washing, IgG goat anti-rabbit IgG (heavy and light chains) conjugated to peroxidase (Capel Laboratories, Cochranville, PA) and diluted 1:500 in PBS-T was added, and incubated for 40 minutes at 37° C. The remainder of the test was carried out as described in Example I.

RESULTS

Microbiological culture

*S. aureus* and *Str. agalactiae* were not isolated from the lacteal secretions of any cows during the experimental period. Stphylococcus species other than *S. aureus* and Streptococcus species other than *Str. agalactiae* were isolated intermittently. None of these isolates were associated with clinical disease during the experiment and, therefore, were not considered in relation to data processsing.

ELISA results

The results of the ELISA tests are shown in Tables 23–25. The results of the samples taken 1 week prior to inoculation showed that there were detectable levels of specific antibody of all classes present in the 3 groups of cows. The IgG levels in Group 3 were slightly elevated, the difference between these and Group 1 control cows being significant at the 0.02 level for IgG, and at the 0.01 level for $IgG_2$ as computed by teh student t test. IgA and IgM levels did not differ significantly between the groups.

Four weeks after the first inoculation, specific antibodies of all classes were significantly elevated for the 2 groups of vaccinated cows in comparison with the saline control animals. The cows which were inoculated with vaccine emulsified in Freunds incomplete adjuvant showed responses which were 3.4, 2.6, 8.8 and 5.5 fold the basal levels of the control cows for IgA, IgM, $IgG_1$ and $IgG_2$, respectively.

Eight weeks after the first inoculation, IgA levels in Group 2 cows had returned to approximate control values. The IgA levels in Group 3 cows remained elevated to almost 2 times control levels. $IgG_1$ and $IgG_2$ in Group 3 cows were also still significantly raised although in Group 2 cows $IgG_2$ was no longer elevated.

By 18 weeks, Group 2 vaccinates were indistinguishable from the control group for specific antibody in all classes. Cows which received the vaccine plus adjuvant still showed significantly raised levels of IgA, $IgG_1$ and $IgG_2$. These were 1.9, 3.9 and 2.4 fold the control levels, respectively. The levels of IgG in Group 3 had not yet returned to preinoculation levels since prior to vaccination they were 1.9 ($IgG_1$) and 1.8 ($IgG_2$) fold the control group.

TABLE 23

Relative contribution of each class and subclass of Ig in milk to a response specific for staphylococcal α hemolysin[a]. Cows inoculated with saline.

| Sample (Weeks)[b] | Class and Subclass of Antibody | | | |
|---|---|---|---|---|
| | IgA | IgM | $IgG_1$ | $IgG_2$ |
| −1 x̄ | 0.432 | 0.283 | 0.182 | 0.140 |
| S.E. | 0.050 | 0.041 | 0.023 | 0.019 |
| n | 9 | 9 | 9 | 9 |
| +4 x̄ | 0.227 | 0.157 | 0.163 | 0.110 |
| S.E. | 0.019 | 0.025 | 0.021 | 0.017 |
| n | 8 | 8 | 8 | 8 |
| +8 x̄ | 0.258 | 0.190 | 0.189 | 0.152 |
| S.E. | 0.013 | 0.028 | 0.025 | 0.022 |
| n | 6 | 6 | 6 | 6 |
| +18 x̄ | 0.215 | 0.231 | 0.134 | 0.121 |
| S.E. | 0.030 | 0.077 | 0.018 | 0.030 |
| n | 5 | 5 | 5 | 5 |

[a]Results, obtained by means of ELISA, are expressed as absorbance values at 405 nm.
[b]Vaccine administered at time 0 and +3.

TABLE 24

Relative contribution of each class and subclass of Ig in milk to a response specific for staphylococcal α hemolysin[a]. Cows inoculated with vaccine in saline.

| Sample (Weeks)[b] | Class and Subclass of Antibody | | | |
|---|---|---|---|---|
| | IgA | IgM | $IgG_1$ | $IgG_2$ |
| −1 x̄ | 0.349 | 0.257 | 0.208 | 0.132 |
| S.E. | 0.052 | 0.041 | 0.034 | 0.010 |
| n | 8 | 8 | 8 | 8 |
| +4 x̄ | 0.365 | 0.218 | 0.536 | 0.268 |
| S.E. | 0.025 | 0.022 | 0.060 | 0.026 |
| n | 9 | 9 | 9 | 9 |
| +8 x̄ | 0.269 | 0.183 | 0.328 | 0.221 |
| S.E. | 0.025 | 0.021 | 0.049 | 0.025 |
| n | 8 | 8 | 8 | 8 |
| +18 x̄ | 0.262 | 0.154 | 0.203 | 0.114 |
| S.E. | 0.014 | 0.020 | 0.023 | 0.012 |
| n | 7 | 7 | 7 | 7 |

[a]Results obtained by means of ELISA are expressed as absorbance values at 405 nm.
[b]Vaccine administered at time 0 and +3.

TABLE 25

Relative contribution of each class and subclass of Ig in milk to a response specific for staphylococcal α hemolysin[a]. Cows inoculated with vaccine in mineral oil.

| Sample (Weeks)[b] | Class and Subclass of Antibody | | | |
|---|---|---|---|---|
| | IgA | IgM | $IgG_1$ | $IgG_2$ |
| −1 x̄ | 0.471 | 0.302 | 0.340 | 0.256 |
| S.E. | 0.042 | 0.036 | 0.053 | 0.029 |
| n | 9 | 9 | 9 | 9 |
| +4 x̄ | 0.774 | 0.408 | 1.440 | 0.603 |
| S.E. | 0.078 | 0.046 | 0.153 | 0.041 |
| n | 9 | 9 | 9 | 9 |
| +8 x̄ | 0.496 | 0.231 | 0.934 | 0.521 |
| S.E. | 0.032 | 0.026 | 0.061 | 0.038 |
| n | 9 | 9 | 9 | 9 |
| +18 x̄ | 0.419 | 0.246 | 0.522 | 0.292 |
| S.E. | 0.047 | 0.030 | 0.069 | 0.024 |
| n | 9 | 9 | 9 | 9 |

[a]Results obtained by means of ELISA are expressed as absorbance values at 405 nm.
[b]Vaccine administered at time 0 and +3.

DISCUSSION

The parenteral administration of a vaccine which consists of optimal concentrations of antigen and the adjuvant of choice, results in the production of specific antibodies in all classes of Ig.

Freunds incomplete adjuvant has been shown to be particularly efficacious in the immunopotentiation of responses within the $IgG_1$ subclass [Slanetz, Am.J..Vet.Res., 26:688–695 (1965)]. Recent work has shown that cytophilic $IgG_2$ may play an important role in protection, particularly against staphylococcal mastitis [Watson, Immunol., 31:159–165 (1976); Watson, Aus.J..Biol.Sci., 33:403–522 (1980)]. Immunization under the circumstances described resulted in significant elevations of specific $IgG_2$ as well as $IgG_1$.

The explanation for a local response in the lactating mammary gland following parenteral stimulation is highly speculative. Watson et al reported an increase in specific IgA and IgM following parenteral inoculation at the time of mammary involution and suggested that this was likely a result of the massive migration of primed immunocytes into the gland at this stage of the lactation cycle [Slanetz, Am.J.Vet.Res., 26:688–695 (1965)]. The local immune response in the actively lactating cow is considered to be deficient since there are few Ig producing cells demonstrable in the mammary tissue [Watson, Aus.J.Biol.Sci., 33:403–522 (1980)]. It is possible that antigen administered systemically is carried to the mammary gland and primes cells in situ resulting in a local response of specific IgA and IgM.

It has been demonstrated that a sytemically administered vaccine the constituents of which are optimal, can be efficient at both the local and humoral level in stimulating a response. This mode of immunization, therefore, warrants further investigation as a practicable means for vaccination since it obviates the problems associated with interference with the mammary gland itself.

The various S. aureus and Str. agalactiae strains employed herein are available through Cornell University upon request and where indicated have been or are being deposited with the American Type Culture Collection.

We claim:

1. A vaccine effective for the prevention and/or control of gram-positive cocci caused bovine mastitis which comprises:

an active ingredient component containing per dose:
in total combination a bovine mastitis preventing or controlling amount of at least one of (a) or (b):
- (a) at least one *S. aureus* somatic antigen which is an encapsulated antigen derived from a bovine isolated inactivated *S. aureus;* or
- (b) a bovine mastitis preventing or controlling amount of at least one unencapsulated *S. aureus* antigen which is derived from a bovine isolated inactivated *S. aureus;* and
- (c) in total combination a bovine mastitis preventing and controlling amount of at least one of *Str. agalactiae* antigen derived from a bovine isolated inactivated *Str. agalactiae;* the antigen being derived from at least one of inactivated *Str. agalactiae,* Type I (Ia or Ib or Ic or mixtures), Type II and Type III; the amount of each of said *Str. agalactiae* antigen present being an amount sufficient to contribute at least about 17–280 mg N per dose;

said active component being emulsified with sufficient mineral oil to provide enhanced vaccine response when administered to a bovine.

2. A vaccine as in claim 1, wherein the active ingredient component comprises per dose
- (a) in total combination a bovine mastitis preventing or controlling amount of at least one *S. aureus* somatic antigen which is an encapsulated antigen derived from a bovine isolated inactivated *S. aureus;*
- (b) in total combination a bovine mastitis preventing or controlling amount of at least one unencapsulated *S. aureus* antigen which is derived from a bovine isolated inactivated *S. aureus;* the amount of each of (a) and (b) per dose being an amount sufficient to contribute at least about 100–120 mg N per dose;

- (c) in total combination a bovine mastitis preventing or controlling amount of staphylococcal α hemolysin toxoid, in an amount sufficient to contribute about 0.8–1.2 mg N per dose;
- (d) in total combination a bovine mastitis preventing or controlling amount of staphylococcal β hemolysin toxoid, between about 1.3–1.7 mg N per dose;
- (e) in total combination a bovine mastitis preventing or controlling amount of staphylococcal γ hemolysin toxoid, in an amount sufficient to contribute about 0.8–1.2 mg N per dose;
- (f) in total combination a bovine mastitis preventing or controlling amount of staphylococcal derived Leucocidin toxoid, in an amount sufficient to contribute between about 1.3–1.7, 2.5 mg N per dose;
- (g) in total combination a bovine mastitis preventing or controlling amount of *Str. agalactiae* antigens derived from a bovine isolated inactivated *Str. agalactiae;* the antigens being derived from all three of inactivated *Str. agalactiae,* Type I (Ia or Ib or Ic or mixtures), Type II and Type III; the amount of each of said *Str. agalactiae* antigen present usually being an amount sufficient to contribute between about 60–80 mg N per dose.

3. The vaccine of claims 1 or 2, wherein the mineral oil adjuvant contains emulsion enhancing amounts of a physiologically acceptable emulsifying agent.

4. A method of preventing or controlling bovine mastitis in a bovine which comprises administering to said bovine the vaccine of claims 1 or 2.

5. A method as in claim 4, wherein the vaccine is administered a multiplicity of times over spaced intervals.

6. The vaccine of claim 1 wherein the vaccine contains (b) a bovine mastitis preventing or controlling amount of at least one unencapsulated *S. aureus* antigen which is derived from a bovine isolated inactivated *S. aureus.*

* * * * *